(12) United States Patent
Fuji

(10) Patent No.: US 7,582,261 B2
(45) Date of Patent: Sep. 1, 2009

(54) ELECTRICITY SUPPLYING DEVICE, ELECTRICITY SUPPLYING APPARATUS, SAMPLE DETECTION DEVICE, AND SAMPLE DETECTION APPARATUS

(75) Inventor: Hiroshi Fuji, Soraku-gun (JP)

(73) Assignee: Sharp Kabuhsiki Kaisha, Osaka (JP)

( * ) Notice: Subject to any disclaimer, the term of this patent is extended or adjusted under 35 U.S.C. 154(b) by 726 days.

(21) Appl. No.: 10/988,303

(22) Filed: Nov. 12, 2004

(65) Prior Publication Data

US 2005/0106065 A1    May 19, 2005

(30) Foreign Application Priority Data

Nov. 18, 2003  (JP) .............. 2003-388212
Nov. 18, 2003  (JP) .............. 2003-388226
Nov. 18, 2003  (JP) .............. 2003-388245

(51) Int. Cl.
G01N 21/00 (2006.01)
(52) U.S. Cl. .................................. 422/82.11
(58) Field of Classification Search ............... 422/82.11
See application file for complete search history.

(56) References Cited

U.S. PATENT DOCUMENTS

| | | | |
|---|---|---|---|
| 5,591,629 A | 1/1997 | Rodriguez et al. |
| 5,822,285 A | 10/1998 | Rugar et al. |
| 5,855,882 A | 1/1999 | Li et al. |
| 5,861,238 A | 1/1999 | Li et al. |
| 5,891,341 A | 4/1999 | Li et al. |
| 5,962,245 A | 10/1999 | Li et al. |
| 6,132,579 A | 10/2000 | Edwards et al. |
| 6,143,247 A | 11/2000 | Sheppard, Jr. et al. |
| 6,143,248 A | 11/2000 | Kellogg et al. |
| 6,319,468 B1 | 11/2001 | Sheppard, Jr. et al. |
| 6,319,469 B1 | 11/2001 | Mian et al. |
| 2001/0055812 A1 | 12/2001 | Mian et al. |
| 2002/0076804 A1 | 6/2002 | Sheppard et al. |
| 2002/0137218 A1 | 9/2002 | Mian et al. |
| 2002/0150512 A1 | 10/2002 | Kellogg et al. |
| 2002/0164325 A1 | 11/2002 | Rodriguez et al. |
| 2003/0044997 A1 | 3/2003 | Kasahara et al. |
| 2003/0185827 A1 | 10/2003 | Rodriguez et al. |
| 2005/0069913 A1 | 3/2005 | Mian et al. |
| 2006/0035220 A1 | 2/2006 | Tashiro et al. |
| 2006/0140930 A1 | 6/2006 | Rodriguez et al. |
| 2006/0194264 A1 | 8/2006 | Sheppard et al. |

(Continued)

FOREIGN PATENT DOCUMENTS

EP         0934771 A1  *  8/1999

(Continued)

*Primary Examiner*—Walter D Griffin
*Assistant Examiner*—Bobby Ramdhanie
(74) *Attorney, Agent, or Firm*—George W. Neuner; David G. Conlin; Edwards Angell Palmer & Dodge LLP

(57) ABSTRACT

A sample detection device includes a disk substrate which allows a light beam to be transmitted, and the substrate has flow paths each of which allows polymers to be injected therein, wherein the substrate further includes a guiding groove, provided in a perpendicular direction with respect to a longitudinal direction of each flow path, along which the light beam for detecting polymers scans. According to the sample detection device, it is possible to efficiently detect many kinds of polymers in accordance with respective separation rates of the polymers.

7 Claims, 8 Drawing Sheets

U.S. PATENT DOCUMENTS

2007/0190665 A1    8/2007    Kasahara et al.

FOREIGN PATENT DOCUMENTS

| JP | 09-304338 | 11/1997 |
| JP | 10320855 | 12/1998 |
| JP | 2000-310614 A | 11/2000 |
| JP | 2002-503331 | 1/2002 |
| JP | 2002-139418 A | 5/2002 |
| JP | 2003-156442 A | 5/2003 |
| JP | 2003-156471 A | 5/2003 |
| JP | 2003-248006 | 9/2003 |
| JP | 2003-066003 | 3/2005 |
| WO | WO 03/064998 A2 | 8/2003 |
| WO | WO 0306998 A2 * | 8/2003 |

* cited by examiner

ELECTRICITY SUPPLYING DEVICE, ELECTRICITY SUPPLYING APPARATUS, SAMPLE DETECTION DEVICE, AND SAMPLE DETECTION APPARATUS

This Nonprovisional application claims priority under 35 U.S.C. § 119(a) on Patent Application No. 2003/388212 filed in Japan on Nov. 18, 2003, Patent Application No. 2003/388226 filed in Japan on Nov. 18, 2003, Patent Application No. 2003/388245 filed in Japan on Nov. 18, 2003, the entire contents of which are hereby incorporated by reference.

FIELD OF THE INVENTION

The present invention relates to a sample detection device and a sample detection apparatus each of which separates and detects sample liquid such as polymers contained in liquid (hereinafter, referred to as a sample liquid) on the basis of centrifugal separation and electric field effect.

BACKGROUND OF THE INVENTION

Conventionally, in case of analyzing an extremely small amount of polymers such as proteins and nucleic acids (DNA, RNA) contained in liquid, an electrophoresis apparatus has been used, and a liquid separation apparatus and a capillary electrophoresis apparatus are known as typical electrophoresis apparatuses.

A first conventional art for separating polymer components contained in liquid is a liquid separation apparatus and a liquid separation method that are disclosed in Japanese Publication for Unexamined Publication No. 281619/1999 (Tokukaihei 11-281619) (published on Oct. 15, 1999: corresponding to U.S. Pat. No. 6,132,597). The liquid separation apparatus is arranged so that a disk-shape substrate has a plurality of electrophoresis paths (flow paths) for electrophoresis, extending from a center of the disk in all directions, each of which has power source electrodes on its beginning point and termination. When liquid containing polymers are electrophoresed in each of the flow paths, the polymers are separated in terms of a molecular weight and an electrostatic property, and are electrically detected by a detection electrode provided in a vicinity of the termination of the flow path.

Further, a second conventional art for separating polymer components contained in liquid is a capillary electrophoresis apparatus disclosed in Japanese Publication for Unexamined Publication No. 304338/1997 (Tokukaihei 9-304338) (published on Nov. 28, 1997). This apparatus carries out not only the foregoing electrical detection but also fluorescence detection by binding fluorescent materials to polymers and emitting a laser beam or the like. The capillary electrophoresis chip (apparatus) is arranged so that: a position of a laser beam emission spot is fixed in a vicinity of the termination of the flow path, and a time taken for migrating polymers such as proteins and nucleic acids to pass the laser beam emission spot is detected, thereby detecting the polymers. This is based on the following reason: As a molecular weight of a polymer is smaller, the polymer passes faster, so that it is possible to specify a molecular weight and an electrostatic property on the basis of a time taken to pass the laser beam emission spot.

The first conventional art electrically detects polymers, and the second conventional art optically detects polymers. In this manner, they are different from each other, but they are identical with each other in that: a detection member is provided in a vicinity of the termination of the flow path, and the detection is carried out when the target polymer passes the detection section.

However, when target polymers are different from each other in terms of a molecular weight and an electrostatic property, some polymers are separated quickly and other polymers are separated slowly by electrophoresis. Despite of the difference, the detection section of the first and second conventional arts is fixed, so that the detection is not carried out until the polymer reaches the detection section even when the separation is completed quickly. Further, a polymer which is slowly separated reaches the detection section before the separation is completed, so that it is impossible to carry out the separation and detection.

That is, in the conventional sample detection apparatus, the detection member of the detection device is fixed, so that it is difficult to efficiently detect various polymers.

Further, the disk-type sample detection device of the first conventional art is characterized in that: its rotation enables sample liquid to be sequentially injected; it is possible to detect the separation in the flow path; and the like. However, in case of carrying out electrophoresis, it is necessary to supply power to the sample detection device (it is necessary to apply a voltage or to supply a current to the sample detection device), but the first conventional art has no recitation concerning the power supply.

Further, in case of optically detecting polymers by using the sample detection device of the second conventional art, an electrode and a wiring that are provided so as to supply power shield a light path of the light beam, so that it is impossible to efficiently carry out the optical detection for polymers.

Moreover, the first conventional art has the detection section in a vicinity of the termination of the flow path in order to electrically detect polymers, and the detection is completed when a target polymer passes the detection section. However, according to the electrical detection, an amount of a signal is small and an S/N ratio is low, so that it is difficult to sufficiently detect some kinds of polymers.

Then, there was proposed an apparatus which improves the detection sensitivity by raising the S/N ratio in accordance with not the electrical detection but the optical detection. This is the second conventional art. According to the apparatus, a laser beam is emitted onto a polymer migrating in the flow path, and light transmitted from the polymer is detected, so as to raise the S/N ratio, thereby optically detecting the polymer with high sensitivity.

However, the apparatus of the second conventional art is arranged so that: a light path of laser incident light is bent by a first reflection film at a right angle, and the light is transmitted through the polymer, and then the transmitted light is bent by a second reflection film at a right angle, thereby detecting reflected light of the transmitted light. Thus, a light path of incident light and a light path of reflected light of the transmitted light are not identical with each other, so that it is necessary to provide at least two optical systems such as object glasses for incident light and for reflected light. Therefore, a size of the apparatus itself is large.

SUMMARY OF THE INVENTION

An object of the present invention is to provide a sample detection device and a sample detection apparatus each of which can efficiently detect sample liquid containing wide variety of polymers in accordance with respective separation rates of the polymers.

Further, an object of the present invention is to provide (i) a disk-type sample detection device which has an electrode and an electrode wiring for surely and simply supplying power so as to efficiently carry out optical detection and (ii) a sample detection apparatus provided with a connector for supplying power to the sample detection device.

Further, an object of the present invention is to provide a sample detection device and a sample detection apparatus each of which realizes a smaller size by integrating an optical system for incident light with an optical system for reflected light.

In order to solve the foregoing problems, the sample detection device according to the present invention includes a substrate receiving a light beam, said substrate having one or more flow paths each of which allows sample liquid to be injected therein, wherein the substrate further includes guiding means along which the light beam for detecting the sample liquid scans across each of the flow paths.

According to the arrangement, the guiding means along which the light beam for detecting the sample liquid (for example, a sample containing polymers) scans across the flow path is provided on the substrate, so that the light beam can scan along the guiding means by disposing the guiding means in a desired position on the flow path, thereby detecting the sample liquid (for example, polymers) at this time. Thus, a device in which the guiding means is positioned closer to the beginning point of the flow path is used with respect to a polymer whose separation rate is high, so that it is possible to avoid such problem that the polymer is not detected until the polymer reaches the detecting portion even when the separation is completed quickly. As a result, it is possible to efficiently detect the polymer. Further, a device in which the guiding means is positioned closer to the termination of the flow path is used with respect to a polymer whose separation rate is low, so that it is possible to avoid such problem that: the polymer reaches the detecting portion before being separated, so that the separation and detection cannot be carried out. As a result, it is possible to efficiently detect the polymer. That is, the light beam for detecting polymer can scan along the guiding means, so that it is possible to detect a polymer at a desired position.

Further, it is preferable to arrange the sample detection device according to the present invention so that the guiding means is provided so as to cross the flow path substantially in a perpendicular direction with respect to a longitudinal direction of the flow path.

According to the arrangement, it is possible to detect the sample liquid with high accuracy.

Further, it is preferable to arrange the sample detection device according to the present invention so that: the substrate includes the flow paths in plurality, and the guiding means is provided so as to cross the flow paths, and the guiding means includes flow path identification means for identifying one of the flow paths which has been scanned across by the light beam.

According to the arrangement, a single guiding means crosses a plurality of flow paths, so that it is possible to scan the plurality of flow paths at once by causing the light beam to scan along the guiding means. As a result, it is possible to detect the sample liquid (for example, polymers) in the plurality of flow paths substantially at the same time. Further, at this time, the flow path identification means is formed on the guiding means, so that it is possible to detect the polymers while reading the flow path identification information (for example, a flow path number and the like) by causing the light beam to sequentially scan the flow path identification means and the flow paths. Thus, it is possible to surely identify a flow path in which the polymer has been detected.

Further, it is preferable to arrange the sample detection device according to the present invention so that: the guiding means is provided so as to cross the flow paths plural times, and the guiding means includes track identification means for identifying a track of the guiding means which track has allowed the light to scan the flow path.

According to the arrangement, the light beam scans along the guiding means provided on a desired position of the flow path, so that it is possible to scan the desired position of the flow path. Further, at this time, the track identification means is provided on the guiding means, so that it is possible to detect the sample liquid while reading the track identification information (for example, a track number and the like) by causing the light beam to sequentially scan the track identification means and the flow path. Thus, it is possible to surely identify where the sample liquid has been detected in the flow path. Thus, it is possible to allow the light beam to access an arbitrary position between the beginning (beginning point) and the termination (ending point) of the flow path on the basis of the track number, so that it is possible to efficiently detect the sample liquid at an arbitrary position of the flow path in accordance with a type of the sample liquid.

Further, it is preferable to arrange the sample detection device according to the present invention so that: the substrate is formed substantially in a disk shape, and the guiding means is formed in a concentric circle manner or in a spiral manner.

According to the arrangement, the sample detection device is rotated, so that the light beam can scan across the flow path at high speed. Thus, it is possible to detect the sample liquid at high speed, and it is possible to repetitively detect the sample liquid with high efficiency. Further, in order to solve the foregoing problem, a sample detection apparatus according to the present invention is characterized by including: any one of the foregoing sample detection devices; light beam emitting means for emitting the light beam to the sample detection device; light beam scanning means for causing the light beam to scan along the guiding means provided on the sample detection device; optical detection means for detecting any one of reflected light, transmitted light, scattered light, and emitted light, that are obtained upon emitting the light beam to any one of the flow path, the guiding means, the flow path identification means, and the track identification means, that are provided on the sample detection device; and sample detection means for detecting the sample liquid in accordance with optical information that has been detected by the optical detection means.

According to the arrangement, it is possible to efficiently and surely detect the sample liquid by causing the light beam to scan across the flow path at high speed. Further, in case where the sample detection apparatus is arranged so that the sample detection device is detachably installed, it is possible to efficiently detect various kinds of sample liquid merely by changing the sample detection device. That is, it is not necessary to change the sample detection apparatus, and there are prepared a plurality of sample detection devices different from each other in terms of a position of the guiding means and a sample detection device which corresponds to the target sample liquid is installed onto the sample detection apparatus, so that it is possible to efficiently detect the sample liquid. This is advantageous also in terms of the cost. For example, in case of diagnosing a specific disease by examining DNA, a sample detection device whose guiding means is positioned so as to correspond to the detected DNA is used, so that it is possible to provide a detection system which can efficiently detect the sample liquid at low cost without any modification of the sample detection apparatus.

Further, it is preferable to arrange the sample detection apparatus according to the present invention so as to include: flow path identification signal reading means for reading a signal, obtained by causing the light beam to scan the flow paths, so as to obtain flow path identification information indicating one of the flow paths which has been scanned by the light beam; and sample information outputting means for outputting the flow path identification information obtained by the flow path identification signal reading means and sample detection information obtained by the sample detection means so that the flow path identification information corresponds to the sample detection information.

According to the arrangement, it is possible to identify a flow path in which the sample liquid has been detected with high accuracy.

Further, it is preferable to arrange the sample detection apparatus according to the present invention so as to include: track identification signal reading means for reading a signal, obtained by causing the light beam to scan the track identification means provided on the sample detection device, so as to obtain track identification information indicating a track of the guiding means which track the light beam has scanned along; and sample information outputting means for outputting the track identification information obtained by the track identification signal reading means and sample detection information obtained by the sample detection means so that the track identification information corresponds to sample detection information.

According to the arrangement, it is possible to surely identify where the sample liquid has been detected in the flow path. Further, it is possible to allow the light beam to access (scan) an arbitrary position between the beginning point and the termination of the flow path in accordance with the read track identification information (for example, a track number and the like), thereby carrying out the detection at an arbitrary position on the flow path so as to correspond to the sample liquid.

Further, it is preferable to arrange the sample detection apparatus according to the present invention so that the optical detection means includes: a first optical system for condensing any one of the reflected light, the transmitted light, the scattered light, and the emitted light, that are obtained when the light beam scanning means condenses the light beam in the guiding means, so as to lead thus condensed light to a guiding detector; and a second optical system for leading any one of the reflected light, the transmitted light, the scattered light, and the emitted light, that are obtained when the light beam scanning means condenses the light beam in the flow path, to a sample detector.

According to the arrangement, in case where the guiding means and the flow path are disposed at positions different from each other in a light axis direction of the light beam, the first optical system can condense the light beam in the guiding means so that the light beam accesses a desired position, and the second optical system can condense light, that has been reflected or transmitted without being condensed in the flow path, in the sample detector. Thus, it is possible to detect the sample liquid with high accuracy.

In order to solve the foregoing problem, an electricity supplying device according to the present invention is characterized by including: a substrate; a first electrode connection point, provided on the substrate, which supplies a first voltage or a first current that is obtained from electricity supplying means; a second electrode connection point, provided on the substrate, which supplies a second voltage or current; a first electrode wiring connected to a first electrode; and a second electrode wiring connected to a second electrode, wherein the first electrode connection point and the second electrode connection point are provided on vicinities of a center of the substrate so as to be formed substantially in a concentric circle manner so that the first electrode connection point and the second electrode connection point do not electrically contact each other.

According to the arrangement, the power source connector having an electrode for supplying power only to a vicinity of the center is used, so that it is possible to surely and simply supply power. Further, it is possible to supply not only power but also an electronic signal. Further, this arrangement can be used not only in the polymer detection device but also in a device, such as a circuit, whose substrate has other function thereon.

Further, in order to solve the foregoing problem, an electricity supplying apparatus according to the present invention is characterized by including: the foregoing electricity supplying device; an electrical connector for electrically connecting the first electrode connection point to the second electrode connection point that are provided on the electricity supplying device; connection condition detection means for detecting a condition under which the first electrode connection point and the second electrode connection point are electrically connected to each other; and electricity supplying means for supplying a voltage or a current to the first electrode connection point and the second electrode connection point, that are provided on the electricity supplying device, in accordance with an output of the connection condition detection means.

According to the arrangement, it is possible to surely and simply supply electricity, a voltage, or an electronic signal, etc. not only to the polymer detection device but also to various devices.

In order to solve the foregoing problem, a sample detection device according to the present invention is characterized by including a substrate, receiving a light beam, which is formed substantially in a disk shape, said substrate including one or more flow paths each of which allows sample liquid to be injected therein, wherein the substrate includes: a first electrode electrically connected to a termination of each of the flow paths; a second electrode electrically connected to a beginning point of the flow path; a first electrode connection point for supplying a voltage or a current, that is obtained from external power supplying means, to the first electrode; a second electrode connection point for supplying a voltage or a current, that is obtained from the external power supplying means, to the second electrode; a first electrode wiring for electrically connecting the first electrode to the first electrode connection point; and a second electrode wiring for electrically connecting the second electrode to the second electrode connection point, wherein the first electrode connection point and the second electrode connection point are provided on vicinities of a center of the substrate so as to be formed substantially in a concentric circle manner so that the first electrode connection point and the second electrode connection point do not electrically contact each other.

According to the arrangement, the first electrode connection point and the second electrode connection point are collected in a vicinity of the center of the substrate. Thus, the power source connector having an electrode for supplying power only to a vicinity of the center is used, so that it is possible to surely and simply supply power. Further, the power source connector for supplying power can be used also as a turn table or the like on which the disk-type sample detection device is fixed, so that it is possible to reduce the size of the sample detection apparatus.

Further, it is preferable to arrange the sample detection device according to the present invention so that: the first electrode connection point is divided into parts by electrode gaps so as not to electrically contact the second electrode wiring, and the electrode gaps are disposed in all directions at equal rotation angles.

According to the arrangement, it is possible to surely prevent the first electrode connection point and the second electrode connection point from being short-circuited, and it is possible to supply power.

Further, it is preferable to arrange the sample detection device according to the present invention so that: the second electrode connection point is divided into parts by electrode gaps so as not to electrically contact the first electrode wiring, and the electrode gaps are disposed in all directions at equal rotation angles.

According to the arrangement, it is possible to surely prevent the first electrode connection point and the second electrode connection point from being short-circuited, and it is possible to supply power.

Further, it is preferable to arrange the sample detection device according to the present invention so that: the first electrode is provided on a vicinity of a peripheral portion of the substrate so as to be formed substantially in a circular shape, and the first electrode wiring is formed so as to radially extend in a radial direction of the substrate.

According to the arrangement, it is possible to surely prevent the first electrode connection point and the second electrode connection point from being short-circuited, and it is possible to supply power from the first electrode connection point to the first electrode via the first electrode wiring.

Further, it is preferable to arrange the sample detection device according to the present invention so that the first electrode, the second electrode, the first electrode connection point, the second electrode connection point, the first electrode wiring, and the second electrode wiring are provided so as not to overlap the flow paths.

According to the arrangement, it is possible to prevent an electrode or a wiring, provided on the sample detection device, which supplies power, from shielding the light beam, thereby optically detecting polymers with high efficiency.

Further, in order to solve the foregoing problem, a sample detection apparatus according to the present invention is characterized by including: any one of the foregoing sample detection devices; an electrical connector for electrically connecting the first electrode connection point to the second electrode connection point that are provided on the electricity supplying device; connection condition detection means for detecting a condition under which the first electrode connection point and the second electrode connection point are electrically connected to each other; and electricity supplying means for supplying a voltage or a current to the first electrode connection point and the second electrode connection point, that are provided on the electricity supplying device, in accordance with an output of the connection condition detection means.

According to the arrangement, it is possible to surely supply power while preventing the first electrode connection point and the second electrode connection point from being short-circuited. Further, the power source connector for supplying power can be used also as a turn table or the like on which the disk-type sample detection device is fixed, so that it is possible to reduce the size of the sample detection apparatus.

Further, it is preferable to arrange the sample detection device according to the present invention so that in case where the first electrode connection point or the second electrode connection point is divided into n parts by the electrode gaps, the electrical connector has 2n electrical connection points with respect to the first electrode connection point or the second electrode connection point.

Further, it is preferable to arrange the sample detection device according to the present invention so that said 2n electrical connection points are formed in circular shapes, that are identical with each other in terms of a radius, so as to be positioned at equal rotation angles.

Further, it is preferable to arrange the sample detection device according to the present invention so that said 2n electrical connection points provided in the circular shapes alternately have electrical connection with power supplying means different from each other.

According to the arrangement, it is possible to supply power, while surely preventing the first electrode connection point and the second electrode connection point from being short-circuited, without caring for a rotation angle at which the power source connector is installed onto the disk-type sample detection device.

In order to solve the foregoing problem, a sample detection device according to the present invention is characterized by including a substrate receiving a light beam, said substrate including one or more flow paths each of which allows sample liquid to be injected therein, wherein a first reflection film made of dielectric for reflecting the light beam is formed on the substrate so as to be positioned in a rear surface with respect to a surface receiving the light beam so that the first reflection film corresponds to an area having the flow paths.

According to the arrangement, when the light beam for detecting a polymer is emitted to the flow path, a light path of the incident light and a light path of the reflected light correspond to each other. Thus, a single optical system can be used as an optical system for a light beam in an outward route (incident light) and as an optical system for a light beam in a homeward route (reflected light), so that it is possible to easily reduce the size of the sample detection apparatus. Further, after passing (being transmitted) through the flow path, the incident light of the light beam is reflected by the reflection film, and the reflected light passes through the flow path again. Thus, the light beam is transmitted through the polymer migrating in the flow path twice, thereby improving an S/N ratio. Further, the reflection film is made of dielectric, so that it is possible to surely carry out the electrophoresis at high speed without lowering the electric field intensity for the electrophoresis in the flow path.

Further, it is preferable to arrange the sample detection device according to the present invention so that a second reflection film made of metal is formed on the substrate so as to be positioned in the rear surface with respect to the surface receiving the light beam so that the second reflection film is positioned in an area other than an area having the first reflection film.

According to the arrangement, it is possible to radiate heat from the second reflection film portion constituted of a metallic thin film. Thus, it is possible to prevent the temperature of the sample detection device from being raised by Joule heat of the electrophoresis, thereby carrying out the electrophoresis with high accuracy while preventing the polymer from degenerating.

Further, in order to solve the foregoing problem, a sample detection device according to the present invention is characterized by including a substrate receiving a light beam, said substrate including one or more flow paths each of which allows sample liquid to be injected therein, wherein: the substrate includes guiding means along which the light beam for detecting a polymer scans across each of the flow paths, and a first reflection film made of dielectric for reflecting the light beam is formed on the substrate so as to be positioned in a rear surface with respect to a surface receiving the light beam so that the first reflection film corresponds to an area having the flow paths and an area having the guiding means.

According to the arrangement, the guiding means is disposed at a desired position on the flow path, so that the light beam can scan along the guiding means, thereby detecting the polymer at this time. Thus, a device in which the guiding means is positioned closer to the beginning point of the flow path is used with respect to a polymer whose separation rate is high, so that it is possible to avoid such problem that the polymer is not detected until the polymer reaches the detecting portion even when the separation is completed quickly. As a result, it is possible to efficiently detect the polymer. Further, a device in which the guiding means is positioned closer to the termination of the flow path is used with respect to a polymer whose separation rate is low, so that it is possible to avoid such problem that: the polymer reaches the detecting portion before being separated, so that the separation and detection cannot be carried out. As a result, it is possible to efficiently detect the polymer. That is, the light beam for detecting polymers can scan along the guiding means, so that it is possible to detect a polymer at a desired position.

Further, the first reflection film is formed on an area having the flow path and the guiding means. Thus, when the light beam is emitted to the flow path or the guiding means, a light path of the incident light and a light path of the reflected light correspond to each other. Thus, a single optical system can be used as an optical system for a light beam in an outward route (incident light) and as an optical system for a light beam in a homeward route (reflected light), so that it is possible to easily reduce the size of the sample detection apparatus. Further, after passing (being transmitted) through the flow path, the incident light of the light beam is reflected by the reflection film, and the reflected light passes through the flow path again. Thus, the light beam is transmitted through the polymer migrating in the flow path twice, thereby improving an S/N ratio. Further, the reflection film is made of dielectric, so that it is possible to surely carry out the electrophoresis at high speed without lowering the electric field intensity for the electrophoresis in the flow path.

Further, it is preferable to arrange the sample detection device according to the present invention so that a second reflection film made of metal is formed on the substrate so as to be positioned in the rear surface with respect to the surface receiving the light beam so that the second reflection film is positioned in an area other than an area having the first reflection film.

According to the arrangement, a metallic thin film is provided on an area other than an area having the flow path and the guiding means. Thus, it is possible to radiate heat from the second reflection film portion constituted of the metallic thin film. As a result, it is possible to prevent the temperature of the sample detection device from being raised by Joule heat of the electrophoresis, thereby carrying out the electrophoresis with high accuracy while preventing the polymer from degenerating.

Further, it is preferable to arrange the sample detection device according to the present invention so that the first reflection film is constituted of a multi-layered dielectric thin film.

According to the arrangement, high reflectance can be obtained. Thus, reflected light can be efficiently obtained, so that it is possible to surely detect polymers with high accuracy.

Further, in order to solve the foregoing problem, a sample detection apparatus according to the present invention is characterized by including: any one of the foregoing sample detection devices; light beam emitting means for emitting the light beam to the sample detection device; light beam scanning means for causing the light beam to scan along the guiding means provided on the sample detection device; optical detection means for detecting any one of reflected light, transmitted light, scattered light, and emitted light, that are obtained upon emitting the light beam to the flow path or the guiding means; and sample detection means for detecting a polymer in accordance with optical information that has been detected by the optical detection means.

According to the arrangement, the light beam is made to scan across the flow path at high speed, so that it is possible to efficiently and surely detect polymers. Further, in case where the sample detection apparatus is arranged so that the sample detection device is detachably installed, it is possible to efficiently detect various polymers merely by changing the sample detection device. That is, it is not necessary to change the sample detection apparatus, and there are prepared a plurality of sample detection devices different from each other in terms of a position of the guiding means and a sample detection device which corresponds to the target sample liquid is installed onto the sample detection apparatus, so that it is possible to efficiently detect the sample liquid. This is advantageous also in terms of the cost. For example, in case of diagnosing a specific disease by examining DNA, a sample detection device whose guiding means is positioned so as to correspond to the detected DNA is used, so that it is possible to provide a detection system which can efficiently detect the sample liquid at low cost without any modification of the sample detection apparatus.

As described above, the sample detection device or the sample detection apparatus according to the present invention can efficiently separate and detect (i) nucleic acids such as DNA and RNA, (ii) biopolymers such as proteins, and (iii) many other polymers. Thus, in terms of separation and detection of genes and proteins that result in various diseases, the present invention can be used in extremely wide industrial fields such as a medical field, a drug industry, a food industry, and the like.

Further, the sample detection apparatus is arranged so that a single optical system can be used as an optical system for incident light and as an optical system for reflected light. Thus, it is possible to reduce the size of the sample detection apparatus.

For a fuller understanding of the nature and advantages of the invention, reference should be made to the ensuing detailed description taken in conjunction with the accompanying drawings.

DESCRIPTION OF THE EMBODIMENTS

An electricity supplying device and an electricity supplying apparatus according to the present invention have the same characteristics as the sample detection device and the sample detection apparatus. Thus, the following description will explain the sample detection device according to the present invention and will subsequently explain the sample detection apparatus according to the present invention so that also the electricity supplying device and the electricity supplying apparatus are understood without particular explanation thereof. Note that, the present invention is not limited to the following embodiments. Further, the foregoing description exclusively explained the detection of the sample liquid containing mainly polymers. However, as long as a chemical or physical property difference between solvent (e.g., water) and dissolved substances is utilized so as to obtain concentration distribution of the dissolved substances and carry out the detection, similar problems and effects occur. That is, as long as the sample liquid is such that molecules having relatively low molecular weights and dissolved substances such as colloid are dispersed in solvent, the sample detection device and the sample detection apparatus according to the present invention are applicable. That is, the "sample liquid" of the present invention means such sample liquid that molecules having relatively low molecular weights and dissolved substances such as colloid are dispersed in solvent, and the "sample detection" means to detect a sample (dissolved substances, polymers, and the like) contained in the sample liquid. Note that, in order to facilitate the description, a case of detecting polymers from the sample liquid containing the polymers will be described as follows in particular.

[1] As to the sample detection device according to the present invention

Figure 1:
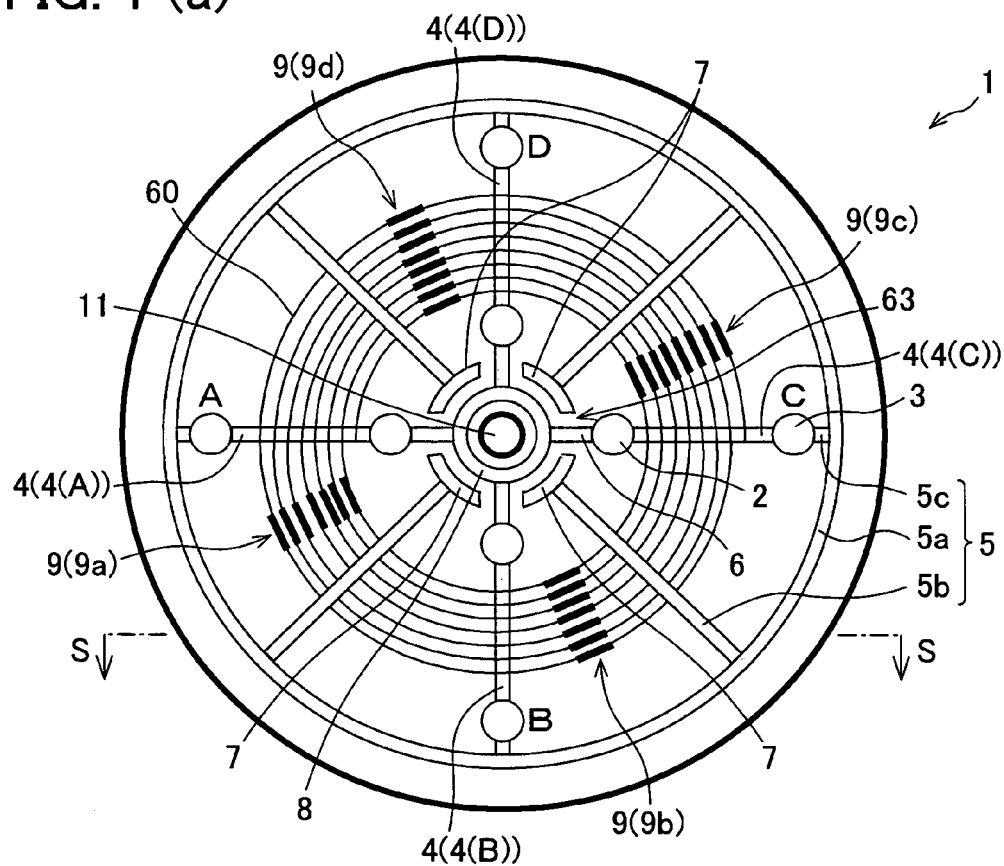
FIG. 1(a) shows a surface (light beam receiving surface) of a sample detection device according to an embodiment of the present invention.
FIG. 1(b) shows a rear surface of the sample detection device shown in FIG. 1(a).
Figure 1:
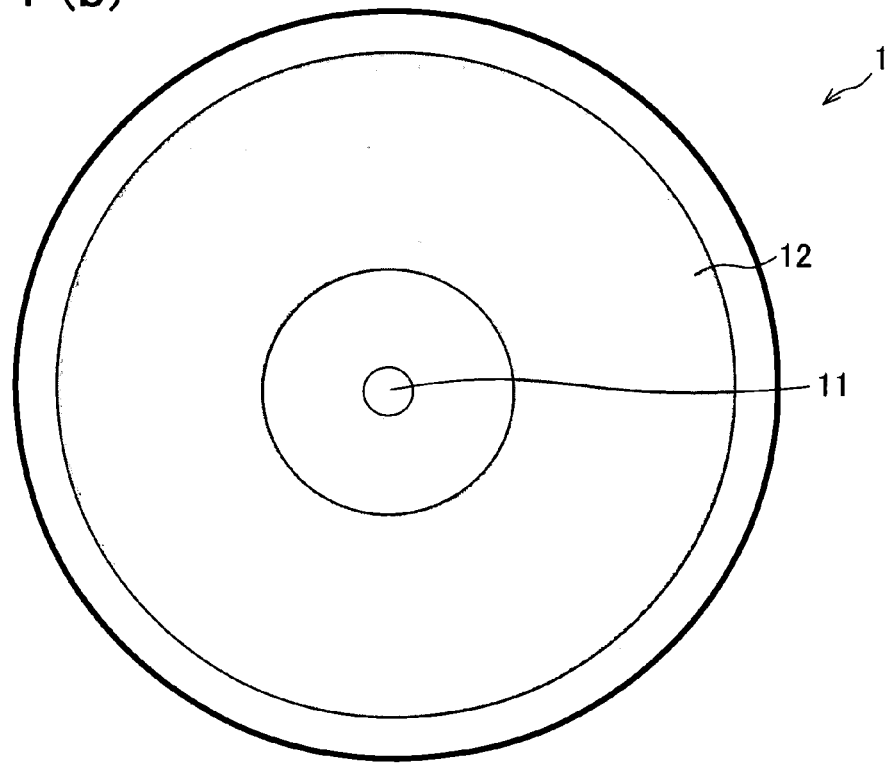
Figure 2:
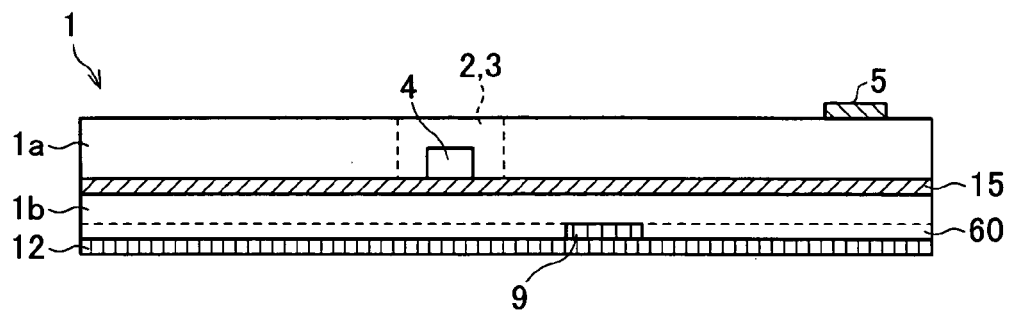
FIG. 2 is a cross sectional view taken along an S-S line of the sample detection device of FIG. 1(a).
Figure 3:
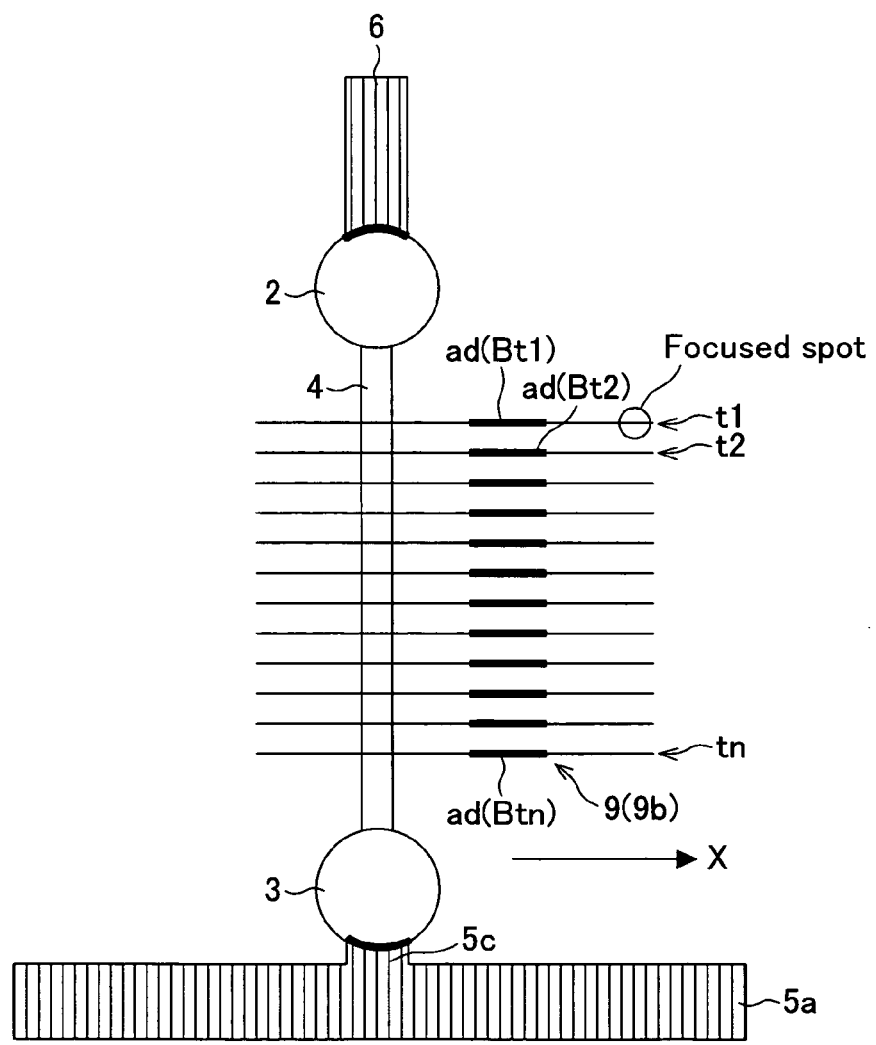
FIG. 3 is a view obtained by partially enlarging a vicinity of a flow path 4(B) of FIG. 1(a).

The following description will explain one embodiment of the sample detection device according to the present invention with reference to FIG. 1 to FIG. 3.

The sample detection device according to the present embodiment includes a substrate to which a light beam is emitted, and flow paths each of which allows sample liquid (for example, sample liquid containing polymers, or similar liquid) to be injected (introduced) therein are formed on the substrate, wherein the substrate has guiding means along which a light beam for detecting sample (for example, polymers) scans across the flow paths. Note that, it is preferable that the substrate allows the light beam to be transmitted.

FIG. 1($a$) is a plan view showing a front surface of the sample detection device (sometimes referred to as a polymer detection device) according to the present embodiment, and FIG. 1($b$) is a plan view showing a rear surface of the sample detection device according to the present embodiment. Further, FIG. 2 is a cross sectional view taken along an S-S line of the sample detection device shown in FIG. 1($a$).

As shown in FIG. 1($a$) and FIG. 1($b$), the sample detection device 1 according to the present embodiment is a disk type. Further, as shown in FIGS. 1 and 2, the sample detection device 1 is arranged so that a disk substrate 1$a$ and a disk substrate 1$b$ are bonded to each other with adhesive 15. Each of the disk substrate 1$a$, the disk substrate 1$b$, and the adhesive 15 has light transmittance which allows a light beam for detecting polymers to be transmitted. Specifically, it is preferable to use a polycarbonate substrate or a glass substrate as the disk substrate 1$a$ and to use a quartz substrate as the disk substrate 1$b$.

The sample detection device 1 includes inlets 2, liquid catchers 3, flow paths 4, first electrodes 5, second electrodes 6, first electrode connection points 7, second electrode connection points 8, address recording sections 9, a central hole 11, a reflection film 12, and a guiding groove 60. The flow paths 4 are four flow paths: a flow path 4(A), a flow path 4(B), a flow path 4(C), and a flow path 4(D). In a corresponding manner, also the address recording sections 9 are four address recording sections: an address recording section 9$a$, an address recording section 9$b$, an address recording section 9$c$, and an address recording section 9$d$. Further, each of the first electrodes 5 is constituted of wiring patterns 5$a$, 5$b$, and 5$c$. Four inlets 2, four liquid catchers 3, four second electrodes 6, four wiring patterns 5$b$, and four wiring patterns 5$c$ are provided so as to correspond to the four flow paths 4. The central hole 11 is formed on centers of the disk substrates 1$a$ and 1$b$ so as to pierce the disk substrates 1$a$ and 1$b$. The central hole 11 determines a center in case of installing an electrophoresis table 50 and a sample detection apparatus 100 that will be described later.

Each of the flow paths 4 is an electrophoresis path for electrophoresing liquid containing polymers so as to separate and extract the polymers, and the flow paths 4 are formed so as to radially extend from the central hole 11 outward in a radius direction. It is preferable that a width of the flow path 4 ranges from several μm to 100 μm and a length of the flow path 4 ranges from several cm to several m. The sample detection device 1 has four flow paths 4, and the flow paths 4 are respectively identified with flow path signs 23 indicated by A to D. As described above, the four flow paths are respectively referred to as the flow path 4(A), the flow path 4(B), the flow path 4(C), and the flow path 4(D). On a beginning point of the flow path 4, there is formed the inlet 2 through which the liquid sample containing polymers is supplied to the flow path 4. On a termination of the flow path 4, the liquid catcher 3 is formed.

Further, the inlet 2 and the liquid catcher 3 are exposed on a surface of the disk substrate 1$a$. As shown in FIG. 2, the flow path 4 is formed by processing a rear surface of the disk substrate 1$a$ so as to shape a hollow-ground downward. Combination of the disk substrate 1$a$ and the disk substrate 1$b$ forms a closed flow path 4.

That is, the flow path 4 is formed on the disk substrate 1$a$ so as to be positioned on a rear surface with respect to a surface having the first electrode 5. The inlet 2 and the liquid catcher 3 are provided on both ends of the flow path 4 so as to pierce the disk substrate 1$a$. On the disk substrate 1$b$, the guiding groove 60 is formed, and the address recording section 9 is formed on a part of the guiding groove 60, and the reflection film 12 is formed thereon. The disk substrate 1$a$ and the disk substrate 1$b$ are combined to each other so that the surface having the flow path 4 contacts a rear surface with respect to a surface having the reflection film 12 with the adhesive 15 therebetween, so that the sample detection device 1 is formed.

Further, the inlet 2 and the liquid catcher 3 are generally used in electrophoresis. Further, the second electrode 6 is connected to the inlet 2, and the first electrode 5 is connected to the liquid catcher 3, more specifically, the wiring pattern 5c is connected to the liquid catcher 3. Thus, in case where a target polymer is DNA for example, a detection condition is as follows. DNA is negatively (−)charged. Thus, when a positive (+) high voltage is applied to the first electrode 5 and the second electrode 6 is grounded, DNA contained in the liquid sample injected from the inlet 2 is pulled toward the first electrode 5 which is a positive (+) side in the flow path 4, so as to be electrophoresed toward the liquid catcher 3. An electrophoresis speed varies depending on a charging amount and a molecular weight of DNA, so that a difference in terms of a traveling speed in the flow path 4 causes DNA to be separated.

Further, the guiding groove 60 is formed on the disk substrate 1b as described above. In more detail, the guiding groove 60 is formed on the disk substrate 1b so as to be positioned on the rear surface with respect to a surface via which the disk substrate 1b contacts the disk substrate 1a. After the guiding groove 60 is formed on the disk substrate 1b, the reflection film 12 is formed so as to cover the guiding groove 60 (see FIG. 2). When a light beam for detecting polymers scans, the guiding groove 60 functions as guiding means for guiding the light beam in carrying out the scanning. That is, the light beam scans the sample detection device along the guiding groove 60. The guiding groove 60 for guiding the light beam in carrying out the scanning is provided in a spiral manner so as to cross the flow paths 4 plural times. In more detail, the guiding groove 60 is provided in a perpendicular direction with respect to a longitudinal direction of the flow path 4 so that the light beam can cross the flow path 4. Here, a direction in which "the light beam crosses the flow path" means a substantially perpendicular direction with respect to a longitudinal direction of the flow path 4.

On a part of the guiding groove 60, the address recording section 9 is formed in an uneven manner. Here, the address recording section 9 functions as flow path identification means for identifying a flow path, which has been crossed by the scanning light beam emitted from the sample detection apparatus 100 described later, out of four flow paths A to D. Moreover, the address recording section 9 functions also as track identification means for identifying a track, along which the light beam has scanned, out of tracks of the guiding groove 60 provided so as to cross the flow paths 4 several times. There are four address recording sections 9a to 9d.

That is, four address recording sections 9a to 9d are provided so as to correspond to the number of the flow paths 4, and flow path identification information of the flow paths 4(A) to 4(D) are stored respectively in the four address recording sections (9a to 9d) respectively adjacent to the flow paths 4(A) to 4(D). That is, an address of the flow path 4(A) is stored in the address recording section 9a, and an address of the flow path 4(B) is stored in the address recording section 9b, and an address of the flow path 4(C) is stored in the address recording section 9c, and an address of the flow path 4(D) is stored in the address recording section 9d. Thus, in case where the light beam scans the flow path 4(A) and the address recording section 9a for example, it is possible to surely confirm that the light beam scans the flow path 4(A). In case where the light beam scans the flow path 4(B) and the address recording section 9b for example, it is possible to surely confirm that the light beam scans the flow path 4(B). Further, guiding groove identification information (for example, a track number) for each track of the guiding groove 60 is stored in each address recording section as described later. Thus, in the address recording sections, an address stored in the guiding groove 60 having the address recording section indicates a flow path identification sign for identifying a flow path and a guiding groove track number for indicating a position of the flow path.

Further, as shown in FIG. 1(b), out of surfaces of the disk substrate 1b, a rear surface with respect to a surface contacting the disk substrate 1a has the reflection film 12. That is, a rear surface with respect to a surface (side) receiving the light beam of the sample detection device 1 has the reflection film 12. The reflection film 12 reflects the light beam projected from an optical pickup device 18 provided on the sample detection apparatus 100 described later, and projects the reflected light to the optical pickup device 18. The optical pickup device 18 detects the reflected light and sends a signal so that other means of the sample detection apparatus 100 detects polymers. Thus, it is possible to detect polymers not with transmitted light but with reflected light, so that it is possible to detect polymers by means of the sample detection apparatus 100 having an optical system provided only on the side receiving the light beam. In case of detecting polymers by detecting transmitted light, it is necessary to dispose optical systems on both sides of the sample detection device 1, so that it is impossible to easily reduce the size of the apparatus itself. While, the reflection film 12 is formed on the rear surface with respect to the surface receiving the light beam of the sample detection device 1, so that it is possible to reflect the incident light beam. As a result, it is possible to detect polymers by detecting the reflected light. Thus, it is possible to produce the sample detection apparatus 100 having an optical system provided only on the side receiving the light beam, thereby easily reducing the size of the apparatus itself.

Further, it is preferable to use not a metallic thin film but a dielectric thin film to form the reflection film 12 as described later. It is well known that it is possible to obtain a high reflectance in case of using a multi-layered thin film in particular. The reflected light is used by means of the reflection film 12 constituted of a dielectric thin film, so that it is possible to reduce the size of the apparatus. Note that, in case of detecting polymers by using transmitted light, the reflection film 12 is not necessary, and the apparatus is not limited to the foregoing arrangement.

Further, the reflection film 12 reflects the light beam emitted to the flow path 4, the guiding groove 60, the address recording section 9 (9a to 9d), and leads the reflected light to the optical pickup device described later. Here, in case of using a reflection film constituted of a metallic thin film such as aluminum and silver in the sample detection device 1 as in the conventional optical disk, the flow path 4 intervenes between the disk substrates 1a and 1b, so that it is impossible to appropriately apply a high electric field, required in electrophoresis, to the flow path 4. That is, an electric conductor (metallic thin film) is disposed so as to cover an underpart of the flow path 4, so that most of the high electric field is applied to a portion between the first electrode 5 and the reflection film constituted of a metallic thin film or a portion between the second electrode 6 and the reflection film constituted of a metallic thin film, so that the high electric field is not applied to a portion between the beginning end and the termination of the flow path 4.

Then, the reflection film 12 is formed as a reflection film constituted of a dielectric thin film, so that an underpart of the flow path 4 functions not as a metal but as a dielectric material, so that it is possible to surely apply the high electric field to a portion between the beginning end and a termination of the flow path 4 without applying the high electric field to the portion between the first electrode 5 and the reflection film 12 or the portion between the second electrode 6 and the reflection film 12. An example of the reflection film constituted of a dielectric thin film is a well-known interference filter. This interference filter is obtained by alternately stacking two types of dielectric thin films which are different from each other in terms of a refraction, and it is possible to set the reflection film as required so as to correspond to a wavelength of a light beam. That is, the reflection film 12 constituted of a dielectric material is formed on the sample detection device 1 so as to be positioned in a rear surface with respect to a surface receiving the light beam so that the reflection film 12 corresponds to an area having the flow path 4. Thus, it is possible to provide a sample detection device which can apply the high electric field to a portion between the beginning end and the termination of the flow path 4 and can reduce the size of the sample detection apparatus 100 using reflected light. Here, "the reflection film 12 constituted of a dielectric material is formed on the sample detection device 1 so as to be positioned in a rear surface with respect to a surface receiving the light beam so that the reflection film 12 corresponds to an area having the flow path 4" means the following arrangement: for example, in the sample detection device 1, the flow path 4 is not formed on the rear surface with respect to the surface receiving the light beam, but the reflection film 12 is formed on the rear surface so as to cover an area having the flow path 4 while corresponding to a shape of the flow path 4 in case where the sample detection device 1 is seen from the rear surface. Note that, the reflection film 12 of the present invention may be arranged in any manner as long as focusing or tracking is carried out by means of the reflected light, and the arrangement is not limited to any specific arrangement.

Figure 9:
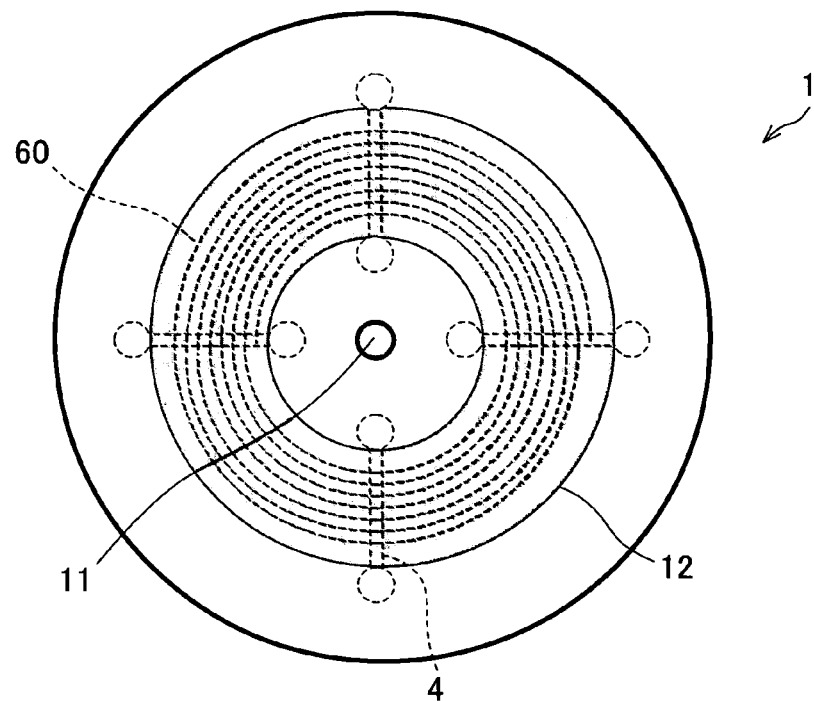
FIG. 9 is a plan view showing a rear surface with respect to a light beam receiving surface of the sample detection device according to the embodiment of the present invention.

Note that, as shown in FIG. 9, as long as the reflection film 12 is formed on the sample detection device 1 so as to be positioned in a rear surface with respect to the surface receiving the light beam so that the reflection film 12 corresponds to at least an area having the flow path 4 and the guiding groove 60, it is not particularly necessary to form the reflection film 12 on other area. That is, as long as the reflection film 12 is formed on the sample detection device 1 so as to be positioned in a rear surface with respect to the surface receiving the light beam so that the reflection film 12 is positioned only in an area scanned by the light beam, it is not particularly necessary to form the reflection film 12 on other area. Here, "the reflection film 12 is formed on the sample detection device 1 so as to be positioned in a rear surface with respect to the surface receiving the light beam so that the reflection film 12 corresponds to at least an area having the flow path 4 and the guiding groove 60" means the following condition: in the sample detection device 1, not the flow path 4 but the guiding groove 60 is formed on the rear surface with respect to the surface receiving the light beam, so that the reflection film 12 is formed on the rear surface so as to cover an area having the flow path 4 and so as to cover an area having the guiding groove 60 while corresponding to a shape of the flow path 4 in case where the sample detection device 1 is seen from the rear surface.

Figure 10:
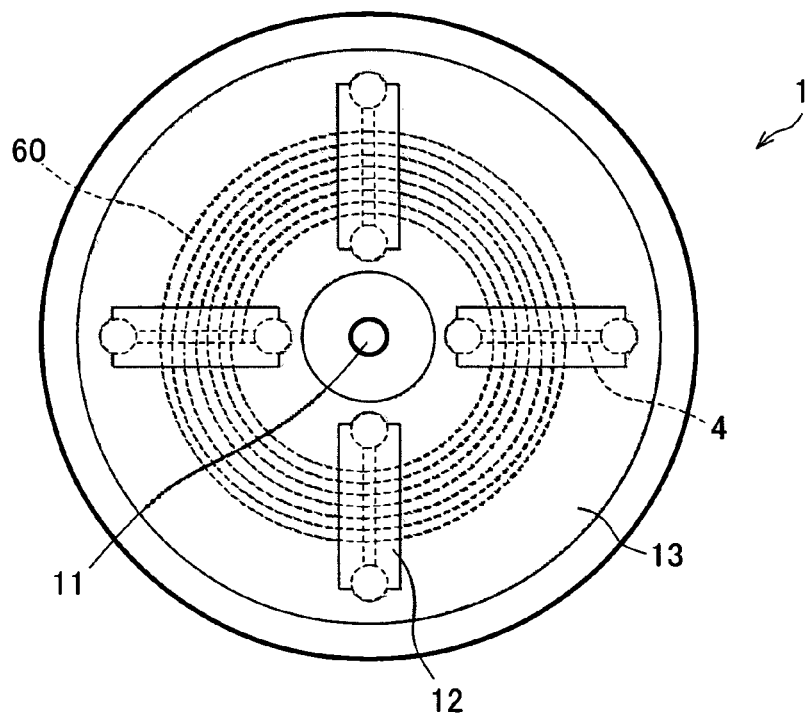
FIG. 10 is a plan view showing a rear surface with respect to a light beam receiving surface of the sample detection device according to the embodiment of the present invention.

Further, as shown in FIG. 10, it may be so arranged that: the reflection film 12 constituted merely of a dielectric thin film is formed merely on an area beneath the flow path 4, and a reflection film 13 constituted of a metallic thin film is formed on other area. That is, it may be so arranged that: the reflection film 12 constituted merely of a dielectric thin film is provided on the sample detection device 1 so as to be positioned in the rear surface with respect to the surface receiving the light beam so that the reflection film 12 corresponds merely to an area having the flow path 4, and the reflection film 13 constituted of a metallic thin film is formed on other area of the rear surface.

In this case, it is necessary to form the reflection film 12 and the reflection film 13 by using different materials, so that it is necessary to carry out an extra step. However, as described below, by forming the reflection film 13 constituted of a metallic thin film, it is possible to prevent heat released by the reflection film 13 from raising temperature of the sample detection device 1. That is, in case of carrying out electrophoresis by applying a high voltage, it is general that Joule heat occurs and temperature of the device rises, which results in deterioration of fluorescent sensitivity or degeneration of polymers.

When a reflection film formed on an area beneath the flow path is the reflection film 12 constituted of a dielectric thin film and a reflection film formed on other area is the reflection film 13 constituted of a metallic thin film as described above, it is possible to enlarge an area of the metallic thin film, so that the metal enables heat to be efficiently released. Thus, it is possible to prevent temperature of the whole sample detection device 1 from rising, thereby minimizing rise of temperature in a part of the flow path 4. Joule heat is in proportion to square of electric field intensity. Thus, in case of applying a high electric field in order to carry out electrophoresis at high speed, particularly great effect can be obtained. Note that, in case of dropping the speed of the electrophoresis, that is, in case of not applying a high electric field, it is not necessary to form the reflection film 13 constituted of a metallic thin film.

Further, the reflection film 12 constituted of a dielectric material is used to reduce the size of the apparatus using reflected light, so that the address recording section 9 (9a to 9d) and the guiding groove 60 that are shown in FIG. 1(a) are not necessarily required. That is, minimum members are the reflection film 12, the flow path 4, the first electrode 5, and the second electrode 6. However, the sample detection device 1 is a disk-type, and the guiding groove 60 is shaped in a spiral manner or in a concentric circle manner, and the address recording section 9 (9a to 9d) is provided, so that it is possible to realize higher speed electrophoresis and higher speed detection carried out after the electrophoresis.

Further, as described above, the flow path 4 formed in a groove shape on the disk substrate 1a so as to be positioned on a surface contacting the disk substrate 1b can be closed by combining the disk substrate 1b to the disk substrate 1a with the adhesive 15 therebetween. Further, each of electrode wirings (for example, the first electrode 5, the second electrode 6, the first electrode connection point 7, and the second electrode connection point 8) are provided on a back surface (rear surface) with respect to a surface having the flow path 4, but this arrangement allows each of the electrode wirings (for example, the first electrode 5, the second electrode 6, the first electrode connection point 7, and the second electrode connection point 8) and the power source connector 30 to be easily connected to each other (see FIG. 2).

Wiring patterns of the first electrode 5, the second electrode 6, the first electrode connection point 7, and the second electrode connection point 8 are described as follows with reference to FIG. 1(a). First, the second electrode connection point 8 is formed substantially in a circular shape in a vicinity of a center of the disk substrate 1a so as not to overlap the flow path 4 and the address recording section 9 and so as to occupy a minimum area. That is, the second electrode connection point 8 is formed substantially in a circular shape so as to be positioned in an innermost circular portion of the disk substrate 1a. The second electrode 6 is provided so as to extend in a radius direction of the disk substrate 1a and so as to electrically connect the inlet 2 to the second electrode connection point 8. That is, four second electrodes 6 are provided substantially in linear shapes so as to correspond to four inlets 2. The second electrode functions also as a second electrode wiring for electrically connecting the inlet 2 which is a beginning point of the flow path 4 to the second electrode connection point 8.

As shown in FIG. 1(a), the first electrode 5 includes: a wiring pattern 5a provided on an outermost circular portion of the disk substrate 1a so as to be substantially in a circular shape; a substantially linear wiring pattern 5b radially provided so as to extend in a radius direction of the disk substrate 1a; a wiring pattern 5c, provided so as to extend in a radius direction of the disk substrate 1a, which electrically connects the wiring pattern 5a to the liquid catcher 3. Each of the wiring pattern 5a, the wiring pattern 5b, and the wiring pattern 5c is provided so as not to overlap the flow path 4 and the address recording section 9 and so as to occupy a minimum area. Each of the wiring patterns 5a and 5c functions as an electrode electrically connected to the liquid catcher 3 which is a termination of the flow path 4. The wiring pattern 5b functions as a first electrode wiring for electrically connecting the foregoing electrodes (the wiring patterns 5a and 5c) to the first electrode connection point 7.

The electrode connection point 7 is provided substantially in a circular shape on the disk substrate 1a so as to be positioned in the outside of the second electrode connection point 8 in a radius direction of the second electrode connection point 8. The electrode connection point 7 is not completely in a circular shape, and has eight electrode gaps 63 so as not to electrically contact four second electrodes 6. That is, it can be said that the first electrode connection point 7 is formed substantially in a circular shape so as to be divided into four parts by eight electrode gaps 63 and four second electrode 6. Further, the second electrodes 6 and the electrode gaps 63 are radially disposed at equal rotation angles. Note that, also the first electrode connection point 7 is provided so as not to overlap the flow path 4 and the address recording section 9 and so as to occupy a minimum area.

The wiring pattern 5a is electrically connected to the first electrode connection point 7 by the wiring pattern 5b. Further, the second electrode 6 is electrically connected to the second electrode connection point 8. An electrophoresis voltage is applied (supplied) to the first electrode connection point 7 and the second electrode connection point 8 by means of the power source connector 30 described later. At this time, both the first electrode connection point 7 and the second electrode connection point 8 are provided in vicinities of the center of the disk substrate 1a (sample detection device), so that it is possible to surely and easily supply the electrophoresis voltage via the power source connector 30 formed in substantially a circular shape.

Further, the address recording section 9 and the guiding groove 60 are provided on the disk substrate 1b so as to be positioned on a rear surface (back side) with respect to a surface contacting the disk substrate 1a, and uneven shapes of the address recording section 9 and the guiding groove 60 do not appear on a flow path surface of the flow path 4 on which the liquid sample flows. In case where the uneven shapes appear in a perpendicular direction with respect to an electrophoresis direction on the flow path surface, there occurs a problem in terms of an electrophoresis property. As described above, the electrode wiring (for example, the first electrode 5, the second electrode 6, the first electrode connection point 7, and the second electrode connection point 8), the flow path 4, the address recording section 9, the guiding groove 60, and the reflection film 12 are respectively disposed with reasonable grounds.

Next, in order to detail the flow path 4, the guiding groove 60, and the address recording sections 9a to 9d which are characteristics of the present invention, FIG. 3 shows a view obtained by partially enlarging a vicinity of the flow path 4(B) of FIG. 1(a).

As shown in FIG. 3, the inlet 2 (an internal portion thereof) is electrically connected to the second electrode 6, and the liquid catcher 3 (an internal portion thereof) is electrically connected to the first electrode 5. In more detail, the liquid catcher 3 is electrically connected to the wiring pattern 5a via the wiring pattern 5c. Thus, as shown by the reference sign 3 in FIG. 1(a), a ground potential is supplied from the second electrode connection point 8 to the inlet 2 via the second electrode 6, and a positive (+) potential is supplied to the liquid catcher 3 via the first electrode 5 (the wiring patterns 5a, 5b, and 5c).

The guiding groove 60 is formed so as to cross the flow paths 4 n times. In view of the vicinities of the flow paths 4, the guiding groove 60 has n tracks. The n tracks of the guiding groove 60 crossing the flow paths 4 are respectively referred to as tracks t1, t2, . . . , and a track tn in such an order that a track nearest to the inlet 2 is the track t1 and a track nearest to the liquid catcher 3 is the track tn.

The address recording sections 9b are formed on parts of the tracks t1 to tn of the guiding groove 60 so as to be positioned in vicinities of the flow path 4(B), and the address recording sections 9b respectively store track information t1 to tn and information of the flow path 4(B), which is flow path identification information, as addresses ad (Bt1) to ad (Btn). For example, in case where the light beam scans the address ad (Bt1), it is possible to confirm that the light beam scans while crossing a track positioned at t1.

When the disk-type sample detection device 1 is rotated in an X direction shown in FIG. 3 and a light beam a is made to scan along the track t1 of the guiding groove 60, the light beam a first scans the address ad (Bt1) so as to read the address ad (Bt1). Thereafter, the light beam a scans crossing a position of the track t1 of the flow path 4(B) so as to detect a polymer. Thus, it is possible to obtain the address before the light beam a scans crossing the position of the track t1 of the flow path 4(B), so that it is possible to confirm a flow path in which the polymer has been detected and to confirm where the polymer has been detected in the flow path with high accuracy.

Further, in case of detecting a polymer such as DNA, it is possible to detect the polymer by carrying out such a general method that a fluorescent material is bound to the polymer such as DNA and the S/N ratio is raised, but it may be so arranged that a coloring material is bound to the polymer and reflected light or transmitted light is detected. Further, when the disk-type sample detection device 1 is rotated at high speed, it is possible to confirm a flow path in which the polymer such as DNA has been detected and to confirm where the polymer such as DNA has been detected in the flow path with high speed.

Further, the guiding groove 60 is formed in a spiral manner, and the guiding groove 60 crosses the four flow paths 4(A) to 4(D) several times. Thus, with rotation of the disk-type sample detection device 1, the tracks of the guiding groove 60 ranging from the track t1 positioned on the side of the inlet 2 to the track tn positioned on the side of the liquid catcher 3 are sequentially scanned, so that it is possible to detect whether the polymer exists or not in each track of all the flow paths 4(A) to 4(D) with high speed and high efficiency.

Further, when a composition of the polymer is known in advance, a desired track in which detection of the composition is expected is accessed out of tracks of the guiding groove 60 and a still operation is carried out, thereby efficiently carrying out the detection. Note that, when a composition of the polymer is known in advance, it is not necessary to form the plural tracks of the guiding groove 60 described above, and a disk-type sample detection device having a single-track guiding groove 60 provided on a desired position may be used. When there are prepared a plural types of disk-type sample detection devices each of which has a single-track guiding groove 60 wherein these devices are different from each other in terms of a radius position (track position), it is possible to carry out the separation and detection covering different polymers. In this case, the sample detection device having the guiding groove 60 can be detachably installed on the sample detection apparatus as described later, so that it is possible to use plural types of disk-type detection devices in a single sample detection apparatus.

[2] As to a sample detection apparatus according to the present invention

The structure of the sample detection device was explained in the foregoing description [1] with reference to FIG. 1 to FIG. 3. The following description will explain a sample detection apparatus provided with the sample detection device, and will explain also operations in using the sample detection apparatus so as to electrophorese polymers and detect thus electrophoresed polymers with reference to FIG. 4 to FIG. 8.

Figure 4:
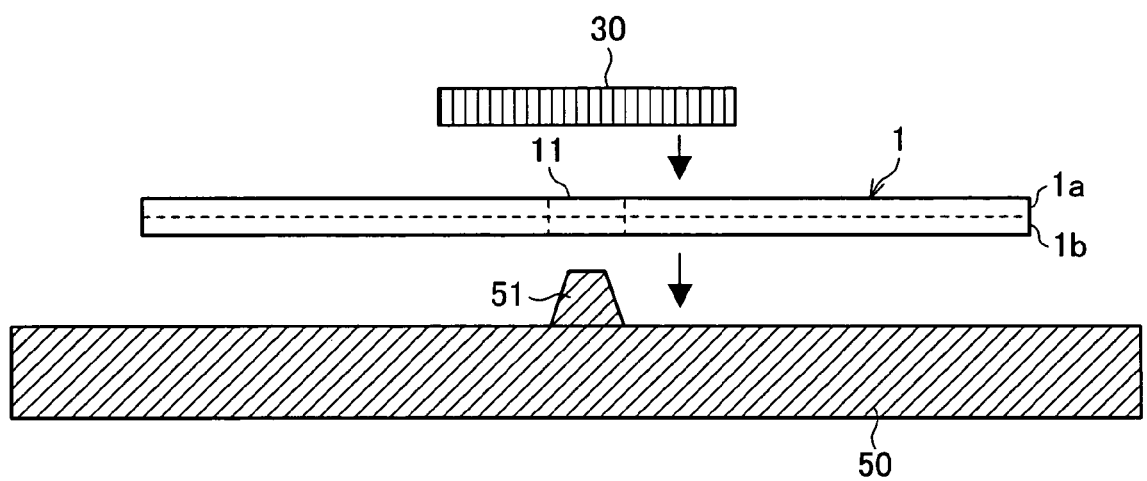
FIG. 4 schematically shows a condition under which the sample detection device according to the embodiment of the present invention is installed on an electrophoresis table.

FIG. 4 schematically shows a condition under which the sample detection device 1 is installed on an electrophoresis table 50 for carrying out electrophoresis. The sample detection device 1 is installed on the electrophoresis table 50, and electrophoresis of polymers is carried out so as to separate and purify the polymers. Thereafter, the sample detection device 1 is installed on the sample detection apparatus 100 described later, so as to detect thus separated and purified polymers by means of a light beam. Note that, it may be so arranged that a device for carrying out the electrophoresis (electrophoresis table 50) and a device for detecting the polymers by means of a light beam are integrated.

In FIG. 4, a protruding portion 51 is formed on the electrophoresis table 50, and the sample detection device 1 is installed on the electrophoresis table 50 so that the protruding portion 51 is engaged in a central hole 11 of the sample detection device 1. As explained in the foregoing description [1], the disk-type sample detection device 1 is obtained by combining the disk substrate 1a with the disk substrate 1b.

Figure 5:
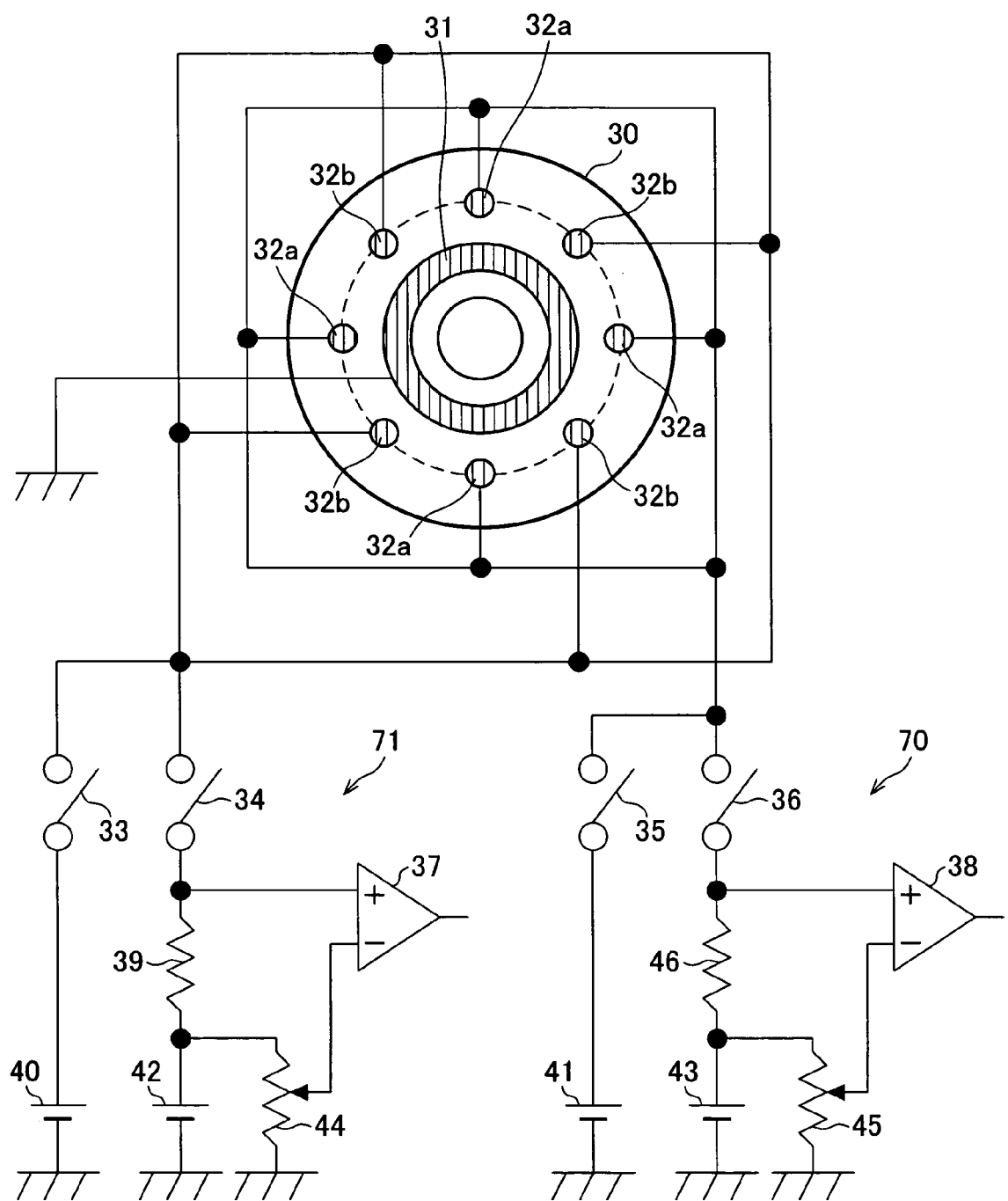
FIG. 5 shows a circuit for supplying power to a power source connector 30 of FIG. 4 and an electrode of the sample detection device.

The protruding portion 51 of the electrophoresis table 50 is engaged in the central hole 11 of the sample detection device 1, so that positioning thereof is performed. Thereafter, the power source connector 30 is made into contact with the sample detection device 1 so as to cover the sample detection device 1, and the power source connector 30 is electrically connected to the first electrode connection point 7 and the second electrode connection point 8 of the sample detection device 1. At this time, the sample detection device 1 is fixed on an arbitrary rotation angle position with respect to a rotation direction, so that it is necessary that the power source connector 30 is electrically connected to the first electrode connection point 7 and the second electrode connection point 8 of the sample detection device 1 so that a voltage can be applied (supplied) without depending on the rotation angle as described later. FIG. 5 schematically shows a condition under which the power source connector 30 is electrically connected to the first electrode connection point 7 and the second electrode connection point 8 of the sample detection device 1 and schematically shows a circuit for supplying power (a circuit for applying a voltage or supplying a current).

As shown in FIG. 5, the power source connector 30 includes a second electrode contact section 31, four first electrode contact sections A 32a·32a·32a·32a, and four first electrode contact sections B 32b·32b·32b·32b. The first electrode contact sections A 32a and the first electrode contact sections B 32b are alternately provided, so as to have the same single radius, at an equal rotation angle.

Further, the second electrode connection section 31 is grounded. While, the four first electrode contact sections A 32a·32a·32a·32a are respectively connected via a switch 35 or a switch 36 to a circuit 70 for supplying power. The four first electrode contact sections B 32b·32b·32b·32b are respectively connected via a switch 33 or a switch 34 to a circuit 71 for supplying power. The circuits 70 and 71 will be detailed later.

The second electrode connection point 8 is electrically connected to a second electrode contact section 31 of the power source connector 30. In more detail, the second electrode contact section 31 is provided on the power source connector 30 so as to be more internally positioned than the first electrode contact sections A 32a or the first electrode contact sections B 32b, and is electrically connected to the second electrode connection point 8 shown in FIG. 1(*a*) so as to overlap the second electrode connection point 8. That is, the second electrode contact section 31 functions as an electrical connection point for supplying a ground potential to the second electrode connection point 8.

While, the first electrode connection point 7 is electrically connected to the first electrode contact section A 32a or the first electrode contact section B 32b of the power source connector 30. In more detail, four first electrode contact sections A 32a and first electrode contact sections B 32b are provided on the power source connector 30 so as to be more externally positioned than the second electrode contact section 31, and are electrically connected to the first electrode connection point 7 shown in FIG. 1(*a*) so as to overlap the first electrode connection point 7. That is, the first electrode contact sections A 32a and the first electrode contact sections B 32b function as connection points each of which supplies a predetermined voltage to the first electrode connection point 7.

The first electrode contact sections A 32a and the first electrode contact sections B 32b are connected to a positive (+) power source without being short-circuited by the switch as described later. At this time, there is a possibility that: the first electrode contact sections A 32a or the first electrode contact sections B 32b may bridge an end of the first electrode connection point 7 and a wiring of the second electrode connection point 6 that are shown in FIG. 1(*a*), which results in short circuit. In order to avoid a problem such as the short circuit, a size of a wiring pattern of the first electrode contact sections A 32a or the first electrode contact sections B 32b is made smaller than the electrode gap 63 between the end of the first electrode connection point 7 and the wiring pattern of the second electrode connection 6 that are shown in FIG. 1(*a*). Further, when a rotation angle at which there is the wiring pattern of the first electrode connection point 7 shown in FIG. 1(*a*) is made larger than 2Π/8, at least one of the first electrode contact sections A 32a or the first electrode contact sections B 32b that are shown in FIG. 1(*a*) is always connected to the first electrode connection point 7. Note that, the foregoing description showed the case where the number of the first electrode connection points 7 is four. However, in case where the number of the first electrode connection points 7 is n (integer number), n first electrode contact sections A 32*a* and n first electrode contact sections B 32*b*, that is, 2n contact sections are provided, and a rotation angle at which there is a pattern of the first electrode connection points 7 shown in FIG. 1(*a*) is made larger than 2Π/2n. By making such arrangement, it is possible to surely prevent the ground potential (the second electrode connection point 6) and the positive potential (an end of the first electrode connection point 7) from being short-circuited even when the power source connector 30 is connected to the sample detection device 1 at an arbitrary rotation angle.

Next, the following description explains a condition under which the first electrode contact sections A 32*a* and the first electrode contact sections B 32*b* are connected to the positive power source without being short-circuited by the switch. As shown in FIG. 5, the first electrode contact section A 32*a* is connected to the circuit 70 via the switch 35 and the switch 36. In more detail, the first electrode contact section A 32*a* is electrically connected to the power source 41 via the switch 35, and is electrically connected to the power source 43 via the switch 36. Further, the first electrode contact section B 32*b* is connected to the circuit 71 via the switch 33 or the switch 34. In more detail, the first electrode contact section B 32*b* is electrically connected to the power source 40 via the switch 33, and is electrically connected to the power source 42 via the switch 34. Further, as shown in FIG. 5, in the circuit 71, a predetermined circuit is constituted of a resistor 39, a comparator 37, and a volume 44 between the switch 34 and the power source 42. Further, in the circuit 70, a predetermined circuit is constituted of a resistor 46, a comparator 38, and a volume 45 between the switch 36 and the power source 43. In this manner, the first electrode contact sections A 32*a* and the first electrode contact sections B 32*b* that are provided so as to be alternately positioned in the same radius at equal rotation angles are electrically connected to respective power supplying means. A condition under which the first electrode contact sections A 32*a* and the first electrode contact sections B 32*b* are connected to the positive power source without being short-circuited by any switch is described as follows.

First, all the switches 33, 34, 35, and 36 are turned OFF. Subsequently, the switch 36 is turned ON. At this time, the first electrode contact sections A 32*a* are under one condition out of (i) a condition under which the first electrode contact sections A 32*a* are electrically connected to the first electrode contact point 7 shown in FIG. 1(*a*), (ii) a condition under which the first electrode contact sections A 32*a* are electrically connected to wiring portions of the second electrode 6, and (iii) a condition under which the first electrode contact sections A 32*a* are electrically connected to none of them.

In case where the first electrode contact sections A 32*a* are electrically connected to the first electrode contact point 7, this condition corresponds to a condition under which the first electrode contact sections A 32*a* are electrically connected also to the first electrode contact sections B 32*b* via the first electrode contact point 7 or a condition under which the first electrode contact sections A 32*a* are merely connected to the first electrode contact point 7. At this time, the first electrode contact sections A 32*a* are electrically connected to the first electrode contact point 7 in any case. Under this condition, there is no path which allows a current to flow via the switch 36. When the volume 45 is adjusted to approximately the middle in advance, a voltage V of the power source 43 is supplied to a positive input of the comparator 38 via the resistor 46. While, a voltage of ½V is supplied to a negative input of the comparator 38. Thus, an output of the comparator 38 becomes high level. That is, in case where the first electrode contact sections A 32*a* are always electrically connected to the first electrode connection point 7 of FIG. 1(*a*), an output of the comparator 38 becomes high level.

While, in case where the first electrode contact sections A 32*a* are in contact with the wiring portions of the second electrode 6 shown in FIG. 1(*a*), the first electrode contact sections A 32*a* are grounded via the second electrode contact sections 31. Thus, in this case, a current flows via the switch 36, and a positive input of the comparator 38 has a ground potential. Thus, an output of the comparator 38 becomes low level. That is, in case where the first electrode contact sections A 32*a* are erroneously in electrical contact with the wiring portions of the second electrode 6 shown in FIG. 1(*a*), the output of the comparator 38 becomes low level.

Further, in case where the first electrode contact sections A 32*a* are connected to none of the wirings of FIG. 1(*a*), a voltage V of the power source 43 is supplied to the positive input of the comparator 38 via the resistor 46. Thus, the output of the comparator 38 becomes high level. That is, in case where the first electrode contact sections A 32*a* are connected to none of the wirings, the output of the comparator 38 becomes high level.

Conclusion of the foregoing three points is as follows: when the output of the comparator 38 is high level, the switch 36 is turned OFF, and then the switch 35 is turned ON, so as to supply a positive potential from the electrophoresis power source 41. This results in either a condition under which power is normally supplied to the first electrode contact points 7 of FIG. 1(*a*) or a release condition under which no power is supplied. Further, when the output of the comparator 38 is low level, the switch 36 is turned OFF, and the switch 35 is kept OFF. This prevents the electrophoresis power source 41 from being erroneously short-circuited to a ground potential via the second electrode contact section 31.

Next, variations of connection of the first electrode contact sections B 32*b* are described as follows. The description is substantially the same as in the case of the first electrode contact sections A 32*a*, and they are different from each other merely in terms of the reference signs, so that detail description thereof is omitted, and only conclusion thereof is given. That is, in case where the output of the comparator 37 is high level, the switch 34 is turned ON after turning OFF the switch 33, so as to supply a positive potential from the electrophoresis power source 42 to the first electrode contact sections B 32*b*. This results in either a condition under which power is normally supplied to the first electrode connection point 7 shown in FIG. 1(*a*) or a release condition under which the first electrode contact sections B 32*b* are not connected to any portion. While, in case where the output of the comparator 37 is low level, the switch 33 is turned OFF, and the switch 34 is kept OFF, so that it is possible to prevent the electrophoresis power source 42 from erroneously being short-circuited to a ground potential via the second electrode contact section 31.

Here, the power source 40 and the power source 41 were separately described, but a single power source may be used as the foregoing power sources. Further, according to the wiring pattern of the power source connector 30 and a pattern arrangement of the first electrode connection point 7 and the second electrode 6, the first electrode contact sections A 32*a* and the first electrode contact sections B 32*b* are not simultaneously released, and at least either the first electrode contact sections A 32*a* or the first electrode contact sections B 32*b* are connected to the power source 40 or the power source 41.

The foregoing description is summarized as follows: in case of connecting the power source connector 30 to the sample detection device 1 by controlling the switches 33 to 36 in accordance with output signals of the comparator 37 and the comparator 38, it is possible to normally supply power to the first electrode connection point 7 of FIG. 1(a) while preventing the short circuit without depending on relative rotation angles. Note that, the switch is controlled by a control circuit (not shown). The circuits 70, 71, and the control circuit (not shown) function as connection condition detection means for detecting a condition under which the first electrode connection point 7 and the second electrode connection points 8 are electrically connected to the power source connector 30 (electrical connection points of the power source connector 30).

Note that, (i) the power source connector 30 shown in FIG. 5 and a peripheral circuit thereof and (ii) the first electrode connection point 7 and the second electrode connection point 8 that are shown in FIG. 1(a) are effective in carrying out electrophoresis in a disk-shaped sample detection device 1. Thus, the guiding groove 60 and the address recording section 9 (9a to 9d) that are shown in FIG. 1(a) are not necessarily required.

Figure 6:
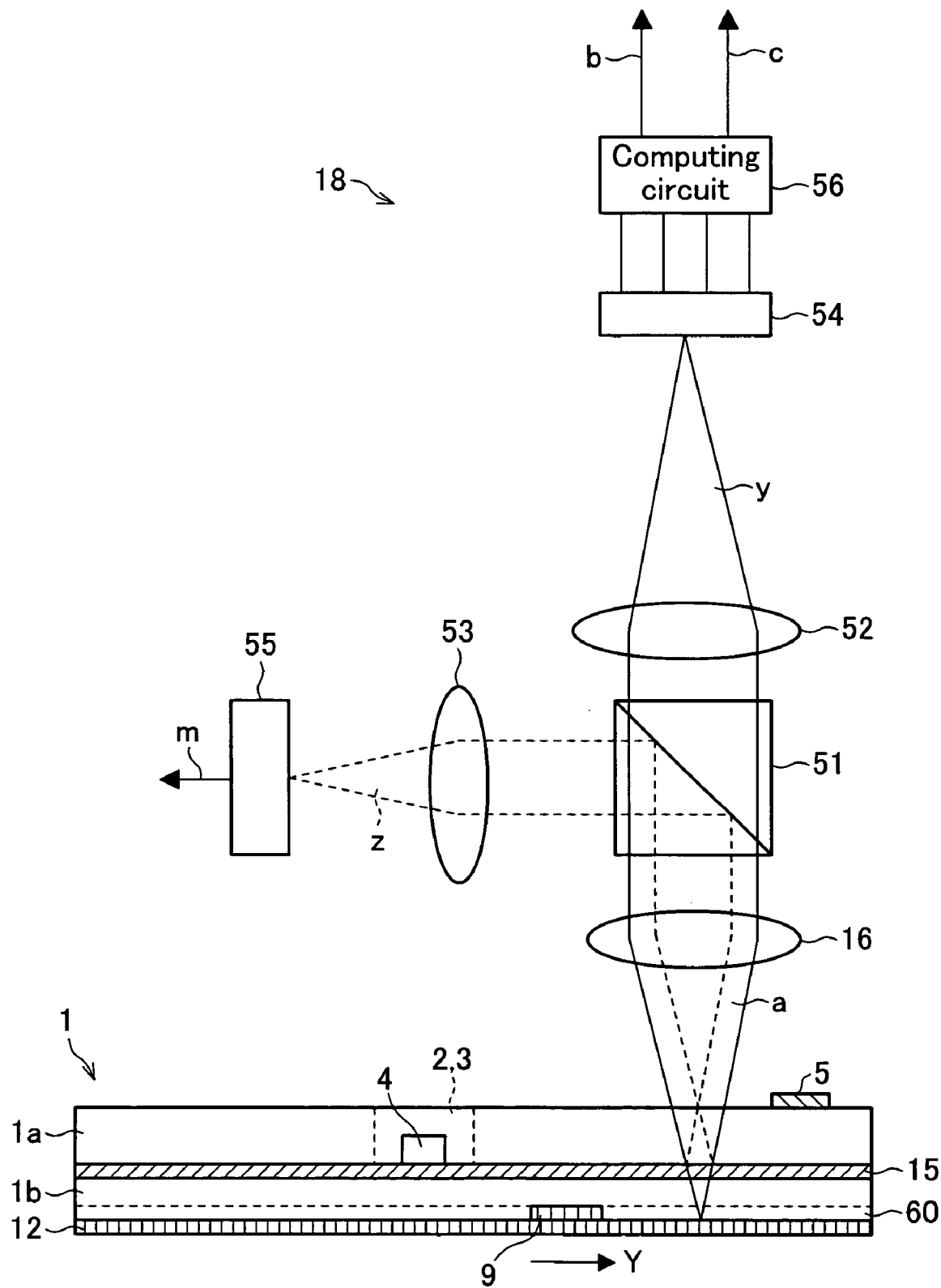
FIG. 6 shows a partially cross sectional view of the sample detection device according to the embodiment of the present invention and a schematic showing a main portion of an optical system for detecting reflected light in an optical pickup device.

Further, FIG. 6 shows a part of a cross sectional view of the sample detection device 1 and shows an important portion of an optical system for detecting reflected light in an optical pickup device 18 which emits a light beam a so as to detect reflected light, transmitted light, or emitted light. Here, in the present embodiment, the optical pickup device 18 functions as optical detection means for detecting any one of reflected light, transmitted light, scattered light, and emitted light that are obtained in emitting the light beam a to any one of the flow path 4, the guiding groove 60, and the address recording section (the flow path identification means or the track identification means) 9 that are provided in the sample detection device 1.

Further, in the disk substrate 1a, a top surface, that is, a surface receiving the light beam has the first electrode 5 and the second electrode 6 (not shown). FIG. 6 shows only the first electrode 5 so as to illustrate a condition under which polymers are detected while the light beam a is scanning the guiding groove 60. Further, in case where a wavelength of laser used as the light beam a is 780 nm and a numerical aperture of the objective lens 16 is 0.45, a thickness of the disk substrate 1a is 0.6 mm and also a thickness of the disk substrate 1b is 0.6 mm. In case where the wavelength of laser used as the light beam a is 650 nm and the numerical aperture of the objective lens 16 is 0.6, the thickness of the disk substrate 1a is 0.3 mm and also the thickness of the disk substrate 1b is 0.3 mm. In case where the wavelength of laser used as the light beam a is 400 nm and the numerical aperture of the objective lens 16 is 0.65, the thickness of the disk substrate 1a is 0.3 mm and also the thickness of the disk substrate 1b is 0.3 mm. In any case, a thickness of the adhesive 15 is dozens μm, and a thickness of the whole sample detection device 1 is within an error range.

As shown in FIG. 6, the optical system of the optical pickup device 18 includes the objective lens 16, a half mirror 51, condenser lenses 52 and 53, a divisional detector 54, a detector 55, and a computing circuit 56. The optical pickup device 18 is arranged so that: the light beam a is condensed by the objective lens 16 so as to be focused on the guiding groove 60 and the address recording section 9 as shown by a continuous line, and a scanning pitch of the light beam a is raised, and scanning accuracy is raised, and an address stored in a high-density manner is read out. Note that, in case of a conventional optical disk, a pitch of the guiding groove 60 is not set to be 1 to 2 μm but is set to be 10 μm or more so as to carry out the scanning while crossing the flow path 4 at high speed. A width of the guiding groove 60 is set to be 1 μm or less as in the conventional optical disk.

The incident light beam a passes through the transparent disk substrate 1a, the transparent adhesive 15, and the transparent disk substrate 1b, and is condensed in the guiding groove 60 and the address recording section 9, and is reflected by the reflection film 12. The reflected light beam (referred to also as reflected light) y is focused on the divisional detector 54 through the objective lens 16, the half mirror 51, and the condenser lens 52 of the optical system of the optical pickup device 18. An output of the divisional detector 54 is appropriately computed in the computing circuit 56, so that a focus error signal and a track error signal b are obtained, thereby carrying out focus servo and track servo in accordance with the focus error signal and the track error signal b. Further, it is possible to read out an address stored in the address recording section 9 in accordance with a signal c obtained by summing and amplifying an output of the divisional detector 54. The arrangement of the optical system is referred to as a first optical system. That is, it can be said that: the first optical system includes the optical pickup device 18, wherein in case where a light beam scanning device (not shown) condenses the light beam a in the guiding groove 60 or the address recording section 9, the light beam scanning device (not shown) condenses any one of reflected light, transmitted light, scattered light, and emitted light that are obtained from the guiding groove 60 or the address recording section 9 so as to lead thus condensed light to the divisional detector 54 (guiding detector). Note that, in the present embodiment, the optical system covers particularly the reflected light or the emitted light. Further, the focus servo, the track servo, and the method and means for reading out the address are well known techniques concerning the optical disk device. That is, as the focus servo, the track servo, and the method and means for reading out the address, conventionally known method and means can be applied, and they are not particularly limited. Further, it is possible to use a conventionally known technique as the light beam scanning means for causing the light beam a to scan, and this is not particularly limited.

Further, the sample detection device 1 rotationally moves in Y direction of FIG. 6, so that the light beam a reaches the flow path 4. When the light beam a reaches the flow path 4, a light path of reflected light y varies as shown by a broken line of FIG. 6. As a result, the light is not focused on the divisional detector 54, so that light intensity detected in the divisional detector 54 greatly drops. Thus, the reflected light or the emitted light cannot be detected in the flow path 4.

In order to solve such a problem, the light path is divided by the half mirror 51, and a second optical system is disposed so that the light is focused on the detector 55 via the condenser lens 53. In the second optical system, the detector 55 detects a light beam z reflected by the flow path 4 and converts thus detected light beam z into an electrical signal so as to output a sample detected signal m. Note that, in case where the light beam is focused on the guiding groove 60 and the address recording section 9, the light beam is focused on the divisional detector 54 and is not focused on the detector 55 as described above, so that an output of the detector 55 greatly drops. That is, it can be said that: the second optical system is provided on the optical pickup device 18, wherein in case where the light beam scanning device (not shown) condenses the light beam a in the flow path 4, the second optical system leads any one of reflected light, transmitted light, scattered light, and emitted light, that are obtained from the flow path 4, to the detector (sample detector) 55.

As described above, even when a focal distance at which the light beam a reaches the flow path 4 does not correspond to a focal distance at which the light beam a reaches the address recording section 9 and the guiding groove 60, it is possible to exactly detect and reproduce them respectively by preparing two optical systems. That is, the optical pickup device 18 according to the present embodiment includes an optical system (second optical system) for detecting a light intensity of a polymer in the flow path 4 and an optical system (first optical system) for condensing light in the guiding groove 60 and the address recording section 9. Note that, the detector 55 does not have to detect an analysis pattern, so that it is not necessary to use a divided optical system. As described above, an outward route (incident light) of the light beam a and a homeward route (reflected light) of the light beam a correspond to each other, and a large part of the optical system can be shared, so that it is possible to reduce the size of the apparatus.

Figure 7:
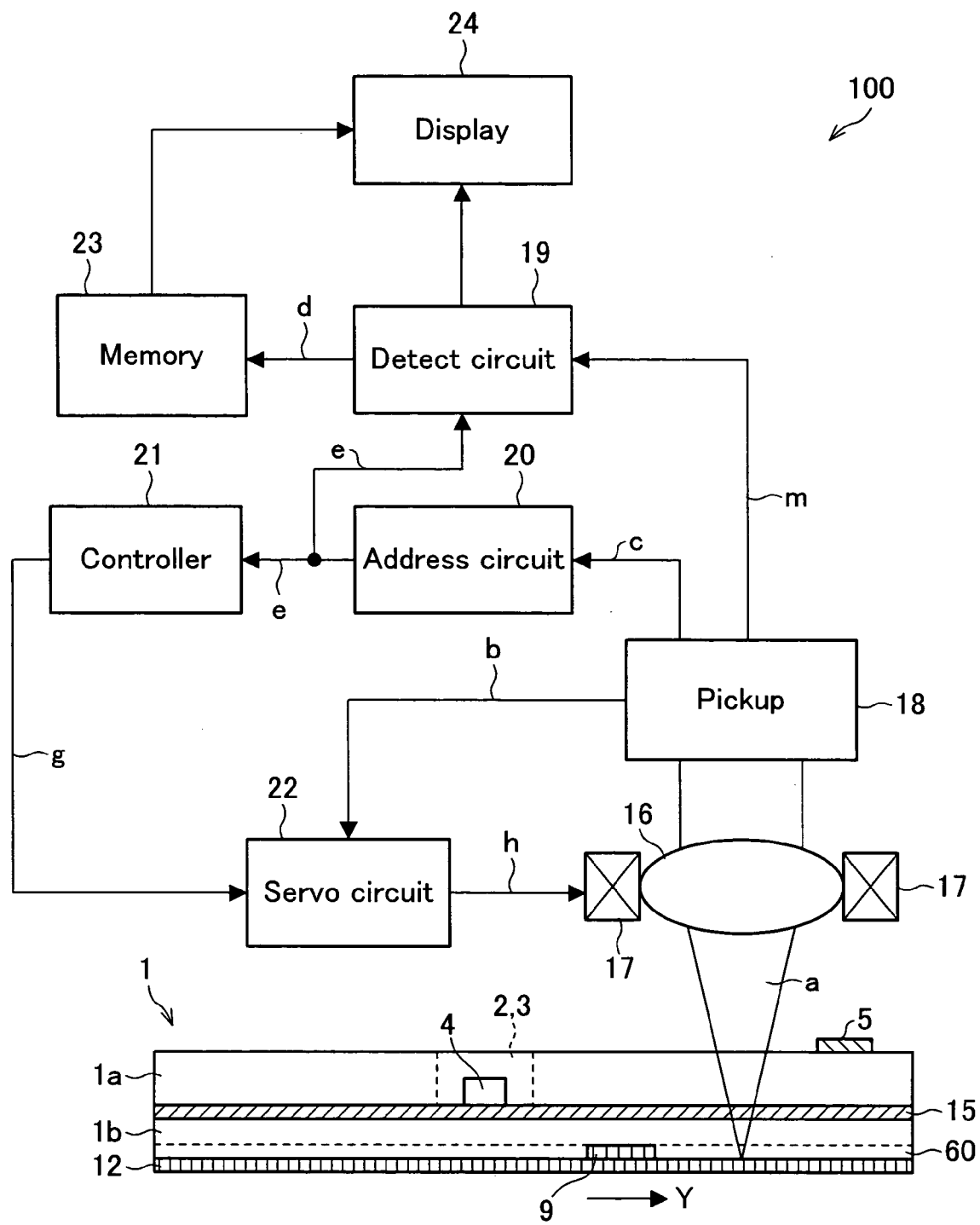
FIG. 7 is a block diagram showing a main portion of the sample detection device according to the embodiment of the present invention.

Further, FIG. 7 is a block diagram showing an important portion of the sample detection apparatus 100 according to the present embodiment. As shown in FIG. 7, the sample detection apparatus 100 includes the optical pickup device 18 provided with the objective lens 16, an actuator 17, a detect circuit 19, an address circuit 20, a controller 21, a servo circuit 22, a memory 23, and a display 24. Here, the detect circuit 19 functions as sample detection means for detecting polymers in accordance with optical information obtained as a result of detection performed by the optical pickup device 18. Further, the address circuit 20 functions as (i) flow path identification signal reading means for reading a signal obtained by causing the light beam a to scan the address recording section (flow path identification means) 9 and for obtaining flow path identification information indicating a flow path (out of the flow paths 4(A) to 4(D)) that has been scanned across by the light beam a and (ii) track identification signal reading means for reading a signal obtained by causing the light beam a to scan and for obtaining track identification information indicating which track of the guiding groove 60 the light beam a has scanned. Further, the display 24 functions as sample information output means for outputting an address (flow path identification information, track identification information, and the like) obtained by the address circuit 20 and polymer detection information obtained by the detect circuit 19 with them corresponding to each other.

Specific functions of an important portion of the sample detection apparatus 100 are described as follows. First, the light beam a emitted from the optical pickup device 18 is condensed by the objective lens 16, and is condensed in the guiding groove 60 or the address recording section 9 of the sample detection device 1. The reflected light from the guiding groove 60 or the address recording section 9 returns to the optical pickup device 18, and a focus error signal/track error signal b, an address signal c, and a sample detected signal m are outputted as shown in FIG. 6.

The focus error signal/track error signal b are fedback to the actuator 17 via the servo circuit 22, and a focus servo process and a track servo process are carried out. The address signal c is inputted to the address circuit 20, and an address e is sent to the controller 21 and the detect circuit 19. The controller 21 outputs a control signal g to the servo circuit 22 while confirming the address e, and causes the light beam a to access a desired position, or turns ON the servo circuit as described later, or holds this condition. The sample detected signal m is inputted to the detect circuit 19, and polymer detection information d of the address e is outputted.

That is, the detect circuit 19 outputs not only an address such as the flow path identification information (flow path sign and the like) and track identification information (track number indicative of a position on the flow path) but also polymer detection information d. Note that, a level of the sample detected signal m varies due to a fluorescent or coloring material bound to a polymer or due to an optical property of the polymer. Thus, it is preferable that the detect circuit 19 includes an 8-bit A/D conversion circuit (sampling means) for example. Further, the outputted polymer detection information d is stored in the memory 23, and is outputted from the display 24 as required, or is outputted from the detect circuit 19 directly to the display 24.

Note that, in case of a sample detection device having a single-track guiding groove 60, the flow path sign and the polymer detection information are outputted, and it is not necessary to output the track number. While, in case of a sample detection device having a single flow path 4, the track number and the polymer detection information are outputted, and it is not necessary to output the flow path sign. However, in terms of compatibility between the sample detection device having a single flow path 4 or a single-track guiding groove 60 and the sample detection device having a plurality of flow paths 4 or a plural-track guiding groove 60, it is preferable that: also in the sample detection device having a single flow path 4 or a single-track guiding groove 60, an address is stored as in the sample detection device having a plurality of flow paths 4 or a plural-track guiding groove 60, and not only the track number indicating a flow path sign and a position on the flow path but also the polymer detection information are outputted.

Figure 8:
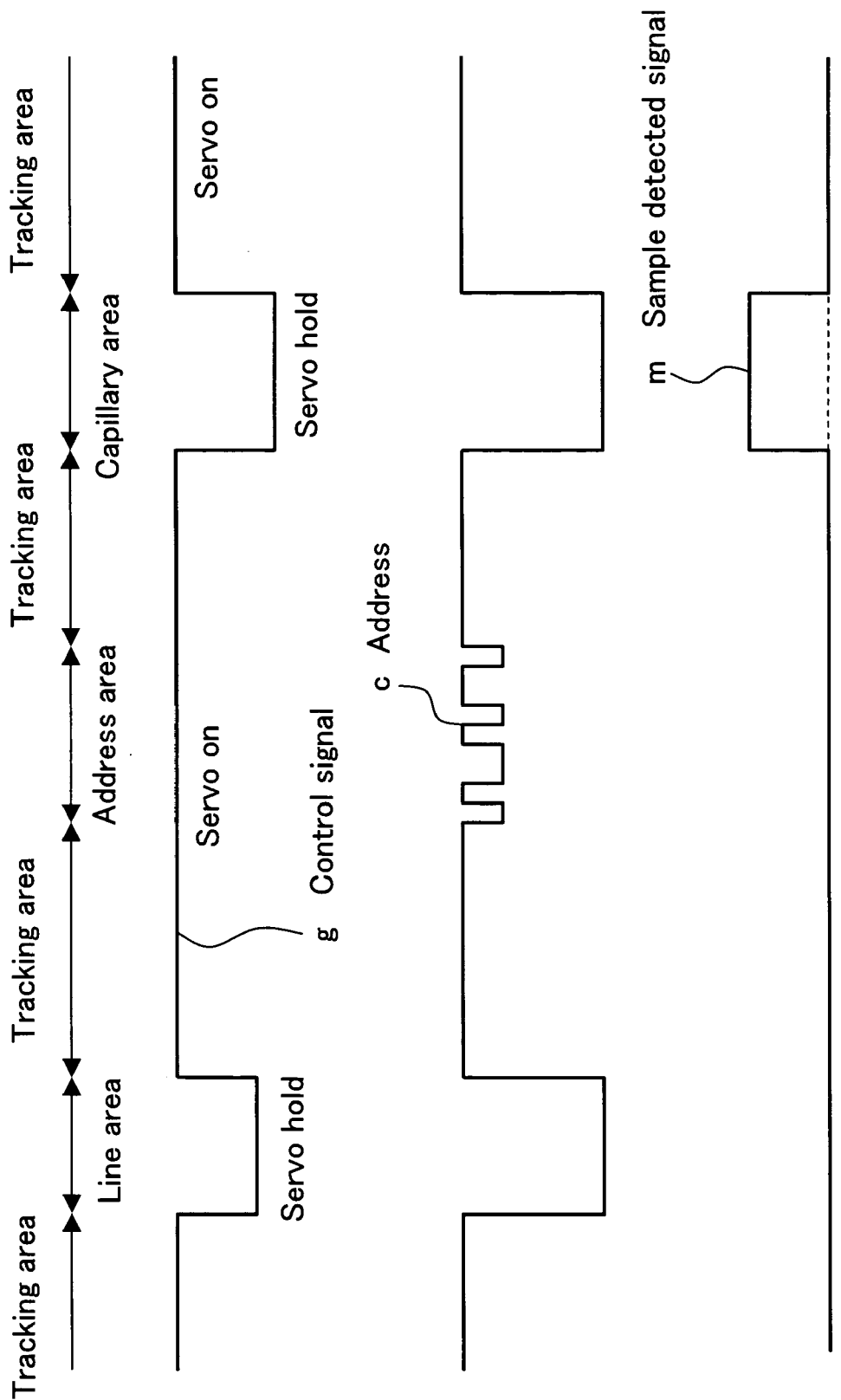
FIG. 8 illustrates timings of an address c, a sample detected signal m, and a control signal g.

Further, FIG. 8 illustrates operation timings of the address signal c, the sample detected signal m, and the control signal g in case where the light beam a scans the guiding groove 60 or the address recording section 9. When the sample detection device 1 moves in Y direction while the light beam a of FIG. 7 is scanning a certain track of the guiding groove 60, at first, the light beam a passes through a tracking area only in the guiding groove 60 as shown in FIG. 8. Further, the light beam a sequentially moves to a wiring area, a tracking area, an address area, a tracking area, a flow path area, and a tracking area of the electrode.

In the first tracking area, the control signal is made high level, and the servo is turned ON. At this time, merely the reading of the guiding groove 60 is carried out, so that the address information signal c is in a constant level. Further, as to the sample detected signal m, light is not condensed in the detector 55 of FIG. 6, so that its voltage is in a low level.

Next, when the light beam a moves to the wiring area, the control signal g is made in a low level, and the servo is held. The light beam a is reflected by the wiring area, and light is not condensed in the divisional detector 54 and the detector 55 that are shown in FIG. 6, so that voltages of both the address information signal and the sample detected signal m become in a low level.

Next, the control signal is made in a high level in the tracking area, and the servo is turned ON. At this time, the address information signal is in a constant level, and a voltage of the sample detected signal m remains in a low level.

Next, when the light beam a moves to the address area, the control signal g is left in a high level, and the servo is turned ON. Analysis is carried out in the address recording section 9 by means of the light beam a, so that an address appears in the address signal c. Further, a voltage of the sample detected signal m remains in a low level.

Next, the control signal g is kept in a high level in the tracking area again, and the servo is turned ON. The address signal c is in a constant level, and a voltage of the sample detected signal m remains in a low level. . Next, when the light beam a moves to the flow path area, the control signal g is made in a low level, and the servo is held. At this time, the light beam a is not condensed in the guiding groove 60, so that the light beam a is not condensed in the divisional detector 54 of FIG. 6. As a result, a voltage of the address signal c is in a low level. However, reflected light from the flow path is condensed in the divisional detector 55, and a voltage level of the sample detected signal m rises as shown by the continuous line due to the reflected light or the emitted light. At this time, the sample detected signal m is sampled by the A/D conversion circuit (sampling means) of the aforementioned detect circuit 19. Note that, in case where no polymer exists in the scanning position of the light beam a, the detection signal is not obtained as shown by the broken line.

Subsequently, the control signal g is kept in a high level in the tracking area again, and the servo is turned ON. At this time, the address signal c is in a constant level, and a voltage of the sample detected signal m remains in a low level.

As described above, the sample detection apparatus 100 according to the present embodiment enables the address e and the sample detected signal m to be read out at high speed while controlling the servo by means of the controller 21, the servo circuit 22, and the actuator 17.

Note that, the foregoing description explained the example where: after electrophoresis is carried out in the electrophoresis table 50, the disk-type sample detection device 1 is moved to the sample detection apparatus 100 having a turn table, and then detection is carried out. However, the present invention is not limited to this example. When the power source connector 30 shown in FIG. 4 and FIG. 5 is used also as the turn table, it is possible to simultaneously carry out the electrophoresis and the polymer detection in the sample detection apparatus 100. Further, it is also possible to carry out the electrophoresis while rotating the disk-type sample detection device 1. That is, it is possible to carry out the high speed access and the scanning of the light beam a while carrying out the electrophoresis, thereby monitoring the polymer detection at real time. Thus, unlike the conventional technique, it is not necessary to wait for the polymer to be electrophoresed at the time of detection, so that it is possible to carry out the high speed electrophoresis and the high speed separation/high speed detection.

Further, as described above, the present embodiment explained the example where polymers are separated by the electrophoresis, but it is possible to use the present invention also in case of separating polymers on the basis of centrifugal separation using a centrifugal force caused by rotation of a disk. In this case, it is not necessary to provide a power source connector, an electrode, and an electrode wiring.

Further, the present embodiment gave description focusing on the disk-type sample detection device 1, but the present invention includes an apparatus which reads a fixed sample detection device of a card type and the like by carrying out laser beam scanning. Also in this case, it is possible to carry out the polymer detection while scanning the aforementioned guiding groove 60 and reading the address. However, compared with the case of using the aforementioned disk-type sample detection device, it is necessary to provide an optical system provided with a laser beam scanning polygon mirror, so that the size of the sample detection apparatus is larger. Thus, an apparatus using the disk-type sample detection device is more preferable since its structure is so simple that it is easy to reduce the size of the apparatus.

Further, the present invention includes a sample detection device which includes: a substrate which allows a light beam to be transmitted; and electrophoresis path means, provided on the substrate, which separates or extracts a polymer, and the sample detection device further includes guiding means along which the light beam scans across the electrophoresis path means.

Further, the present invention includes the sample detection device arranged so that: there are provided the electrophoresis path means in plurality, and a single guiding means is provided so as to cross the plurality of guiding means, and electrophoresis path number means for identifying a number of each electrophoresis path means is provided on the guiding means.

Further, the present invention includes the sample detection device arranged so as to include: a plurality of guiding means which are provided between a beginning point and a termination of the electrophoresis path means; and a track number means, provided on the guiding means, which identifies each of the plurality of guiding means.

Further, the present invention includes the sample detection apparatus which includes: emitting means for condensing the light beam in the sample detection device; scanning means for causing the light beam to scan along the guiding means; optical detection means for detecting reflected light, transmitted light, scattered light, and emitted light from the electrophoresis path means; and sampling means for sampling light intensity that has been detected.

Further, the present invention includes the sample detection apparatus arranged so as to include: electrophoresis path number reading means for reading the electrophoresis path number means; and sample information outputting means for outputting the sampling information and a number of the electrophoresis path with them corresponding to each other.

Further, the present invention includes the sample detection apparatus arranged so as to include: track number reading means for reading the track number means; and sample information outputting means for outputting the polymer information and the track number that have been detected with them corresponding to each other.

Further, the present invention includes the sample detection apparatus arranged so that: the scanning means has a first optical system for condensing the light beam in the guiding means and for condensing transmitted or reflected light from the guiding means so as to lead the condensed light to the guiding detector, and the optical detection means has a second optical system for leading reflected light, transmitted light, or emitted light from the electrophoresis path means to the sample detection detector.

Further, the present invention includes the sample detection device which includes: a disk-shape substrate; and electrophoresis path means, provided on the substrate, which separates or extracts a polymer, wherein the sample detection device further includes: first electrode connection means, disposed at a center of the sample detection device so as to be in a circular shape, which supplies first power; second electrode connection means for supplying second power; electrodes disposed at a beginning point and a termination of the electrophoresis path; first wiring means for connecting the first connection point to the electrode disposed at the beginning point; and second wiring means for connecting the second electrode connection point to the electrode disposed at the termination.

Further, the present invention includes the sample detection device arranged so that: an electrode gap is provided so that at least one of the electrode connection means is divided into parts by the other of the electrode connection means, and the electrode wiring and the electrode gap are radially disposed at equal rotation angles.

Further, the present invention includes the sample detection apparatus which includes: connector means for connecting the first electrode connection means to the second electrode connection means of the sample detection device; connection condition detection means for detecting a condition under which the electrode connection means are connected to the connector means; and power supplying means for supplying a power source voltage or a current to the sample detection device in accordance with an output of the connection condition detection means.

Further, the present invention includes the sample detection apparatus arranged so as to include the connector means having 2N connection points with respect to the electrode connection means divided into N parts.

Further, the present invention includes the sample detection device which includes: a substrate which allows a light beam to be transmitted; and electrophoresis path means, provided on the substrate, which separates or extracts a polymer, wherein the sample detection device includes a first reflection film, made of dielectric for reflecting the light beam, which is positioned at least on a light path of the light beam emitted to the electrophoresis path means.

Further, the present invention includes the sample detection device arranged so as to include a second reflection film, made of metal, which is positioned on a light path other than the first reflection film.

The present invention includes the sample detection device which includes: a substrate which allows a light beam to be transmitted; and electrophoresis path means, provided on the substrate, which separates or extracts a polymer, wherein the sample detection device includes: guiding means along which the light beam scans across the electrophoresis path means; and a first reflection film, made of dielectric for reflecting the light beam, which is positioned at least on a light path of the light beam emitted to the guiding means.

Further, the present invention includes the sample detection device arranged so as to include a second reflection film, made of metal, which is positioned on a light path other than the first reflection film.

Further, the present invention includes the sample detection device arranged so as to include: the guiding means in plurality that are provided between a beginning point and a termination of the electrophoresis path means; and track number identification means, provided on the guiding means, which identifies each of the plurality of guiding means.

The present invention includes the sample detection apparatus which includes: emitting means for condensing the light beam in the sample detection device; scanning means for causing the light beam to scan along the guiding means; optical detection means for detecting reflected light from the electrophoresis path means; and sampling means for sampling the light intensity that has been detected.

Further, the present invention includes the sample detection apparatus arranged so as to include: track number reading means for reading the track number means; sample information outputting means for outputting the polymer information and the track number that have been detected with them corresponding to each other.

Further, the present invention includes the sample detection device arranged so that: the guiding means is provided so as to cross the flow path several times, and the guiding means includes track identification means for identifying a track of the guiding means which track the light has scanned along.

Further, the present invention includes the sample detection apparatus arranged so as to include: flow path identification signal reading means for reading a signal, obtained by causing the light beam to scan the flow paths so as to obtain flow path identification information indicating one of the flow paths which has been scanned by the light beam; and sample information outputting means for outputting the flow path identification information obtained by the flow path identification signal reading means so that the flow path identification information corresponds to sample detection information obtained by the sample detection means.

Further, the present invention includes the sample detection apparatus arranged so as to include: track identification signal reading means for reading a signal obtained by causing the light beam to scan the track identification means provided on the sample detection device so as to obtain track identification information indicating a track of the guiding means which track the light beam has scanned along; and sample information outputting means for outputting the track identification information obtained by the track identification signal reading means so that the track identification information corresponds to sample detection information obtained by the sample detection means.

Further, the present invention is not limited to the aforementioned embodiments, and may be varied in many ways within a scope of the following claims. Embodiments obtained by combining technical means disclosed in different embodiments as required are included in the technical scope of the invention.

Note that, the foregoing embodiments explained only the detection of polymers. However, the present invention is not limited to this, and the present invention is applicable in case of bringing about and detecting concentration distribution of substances dissolved in solvent by utilizing a chemical or physical difference between solvent (for example, water) and substances dissolved therein. For example, the present invention is applicable to sample liquid in which dissolved substances such as molecules whose molecular weights are relatively low or colloids are dispersed.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A sample detection device, comprising a substrate, receiving a light beam, which is formed substantially in a disk shape, said substrate including a center and one or more flow paths, each disposed in a radial direction from the center, and each of which allows sample liquid to be injected therein, wherein the substrate further includes a first electrode, a second electrode, a first electrode connection point and a second electrode connection point, wherein the first electrode connection point and the second electrode connection point are provided in a vicinity of the center substantially in a concentric circular manner so that the first electrode connection point and the second electrode connection point do not electrically contact each other, wherein the first electrode includes a wiring pattern provided on a vicinity of the peripheral portion of the substrate and having a circular shape; a radial wiring pattern extended in a radial direction of the substrate and electrically connecting said wiring pattern and a termination of each of the flow paths; and a first electrode wiring for electrically connecting the first electrode and the first electrode connection point, wherein the second electrode includes a second electrode wiring for electrically connecting the second electrode and the second electrode connection point, said second electrode wiring being electrically connected to a beginning point of the flow path, wherein the first electrode connection point is provided at a position outside of the second electrode connection section in a radial direction, said first electrode connection point is divided into parts by electrode gaps so as not to electrically contact the second electrode wiring, said electrode gaps being disposed radially, and wherein the first electrode does not have electrical contact with the second electrode and the second electrode connection point.

2. The sample detection device as set forth in claim 1, wherein the electrode gaps are disposed in all directions at equal rotation angles.

3. The sample detection device as set forth in claim 1, wherein the first electrode, the second electrode, the first electrode connection point. the second electrode connection point, the first electrode wiring, and the second electrode wiring are provided so as not to overlap the flow paths.

4. A sample detection apparatus, comprising:
the sample detection device as set forth in claim 1;
an electrical connector for electrically connecting the first electrode connection point to
the second electrode connection point that are provided on the electricity supplying device;
connection condition detection means for detecting a condition under which the first electrode connection point and the second electrode connection point are electrically connected to each other; and
electricity supplying means for supplying a voltage or a current to the first electrode connection point and the second electrode connection point that are provided on the electricity supplying device, in accordance with an output of the connection condition detection meant 5. The sample detection apparatus as set forth in claim 4, wherein in case where the first electrode connection point or the second electrode connection point is divided into n parts by the electrode gaps, the electrical connector has 2n electrical connection points with respect to the first electrode connection point or the second electrode connection point, where n is a positive integer.

6. The sample detection apparatus as set forth in claim 5, wherein said 2n electrical connection points are formed in circular shapes, that are identical with each other in terms of a radius, so as to be positioned at equal rotation angles.

7. The sample detection apparatus as set forth in claim 6, wherein said 2n electrical connection points provided in the circular shapes alternately have electrical connection with power supplying means different from each other.

* * * * *

UNITED STATES PATENT AND TRADEMARK OFFICE
CERTIFICATE OF CORRECTION

| | | |
|---|---|---|
| PATENT NO. | : 7,582,261 B2 | Page 1 of 1 |
| APPLICATION NO. | : 10/988303 | |
| DATED | : September 1, 2009 | |
| INVENTOR(S) | : Hiroshi Fuji | |

It is certified that error appears in the above-identified patent and that said Letters Patent is hereby corrected as shown below:

On the Title Page:

The first or sole Notice should read

--subject to any disclaimer, the term of this patent is extended or adjusted under 35 U.S.C. 154(b) by 1236 days.--

Signed and Sealed this

Fourteenth Day of September, 2010

David J. Kappos
*Director of the United States Patent and Trademark Office*